United States Patent [19]

Horwell et al.

[11] Patent Number: 5,554,643

[45] Date of Patent: Sep. 10, 1996

[54] PRO-DRUGS FOR CCK ANTAGONISTS

[75] Inventors: David C. Horwell; Martyn C. Pritchard, both of Cambridge; Reginald S. Richardson, Suffolk, all of England

[73] Assignee: Warner-Lambert Company, Morris Plains, N.J.

[21] Appl. No.: 227,211

[22] Filed: Apr. 13, 1994

Related U.S. Application Data

[60] Division of Ser. No. 726,653, Jul. 12, 1991, Pat. No. 5,340,825, which is a continuation-in-part of Ser. No. 576,315, Aug. 31, 1990, abandoned.

[51] Int. Cl.$^6$ ............... A61K 31/405; C07D 209/18
[52] U.S. Cl. ............................... 514/419; 548/495
[58] Field of Search .................. 548/495; 514/419

[56] References Cited

U.S. PATENT DOCUMENTS

| | | | |
|---|---|---|---|
| 4,164,571 | 8/1979 | Bonfils et al. | 424/177 |
| 4,997,950 | 3/1991 | Murphy et al. | 548/303 |
| 5,278,316 | 1/1994 | Horwell et al. | 514/419 |

FOREIGN PATENT DOCUMENTS

| | | | |
|---|---|---|---|
| 0405537 | 1/1991 | European Pat. Off. | |
| 9100274 | 1/1991 | WIPO | |

OTHER PUBLICATIONS

Voelter et al. CA 94:140148v. 1980.
D. Horwell, et al., *Eur. J. Med. Chem.*, (1990) 25, 53–60.
D. Horwell, et al., *J. Med. Chem.*, 1991, 34, 404–414.
Chemical Abstracts, vol. 109, 1988, p. 666, 109:6970g.
Chemical Abstracts, vol. 113, 1990, p. 715, 113:132771p.

*Primary Examiner*—Jane Fan
*Attorney, Agent, or Firm*—Elizabeth M. Anderson

[57] ABSTRACT

Novel pro-drugs to new and unnatural depeptoids of α-substituted Trp-Phe derivatives useful as agents in the treatment of obesity, hypersecretion of gastric acid in the gut, gastrin-dependent tumors, or as antipsychotics are disclosed. Further, the dipeptoids are antianxiety agents and antiulcer agents. They are agents useful for preventing the response to the withdrawal from chronic treatment or with use of nicotine, diazepam, alcohol, cocaine, caffeine, or opioids. The pro-drugs are also useful in treating and/or preventing panic attacks. Also disclosed are pharmaceutical compositions and methods of treatment using the pro-drugs as well as processes for preparing them and novel intermediates useful in their preparation. An additional feature of the invention is the use of the subject pro-drug compounds in diagnostic compositions.

17 Claims, No Drawings

PRO-DRUGS FOR CCK ANTAGONISTS

CROSS-REFERENCE TO RELATED APPLICATION

This application is a Divisional application of 07/726,653, filed Jul. 12, 1991, now U.S. Pat. No. 5,340,825; which is a continuation-in-part of 07/576,315, filed Aug. 31, 1990, now abandoned.

BACKGROUND OF THE INVENTION

Agents acting at central cholecystokinin (CCK) receptors may induce satiety (Schick, Yaksh and Go, Regulatory Peptides 14:277–291, 1986). They are also expected to act as analgesics (Hill, Hughes and Pittaway, Neuropharmacology 26:289–300, 1987), and as anticonvulsants (MacVicar, Kerrin and Davison, Brain Research 406:130–135, 1987).

Reduced levels of CCK-peptides have been found in the brains of schizophrenic patients compared with controls (Roberts, Ferrier, Lee, Crow, Johnstone, Owens, Bacarese-Hamilton, McGregory, O'Shaughnessey, Polak and Bloom. Brain Research 288:199–211, 1983). It has been proposed that changes in the activity of CCK neurones projecting to the nucleus accumbens may play a role in schizophrenic processes by influencing dopaminergic function (Totterdell and Smith, Neuroscience 19:181–192, 1986). This is consistent with numerous reports that CCK peptides modulate dopaminergic function in the basal ganglia and particularly the nucleus accumbens (Weiss, Tanzer, and Ettenberg, Pharmacology, Biochemistry and Behaviour 30:309–317, 1988; Schneider, Allpert and Iversen, Peptides 4:749–753, 1983. It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, Gastrointestinal Hormones, Ch. 23, pp 529–564, 1980, ed. G. B. J. Glass, Raven Press, N.Y.). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestional tract (Johnson, ibid., pp 507–527), actions which are associated with increased DNA and RNA synthesis. Moreover, gastrin secreting cells are associated with certain gastrointestinal tumors as in the Zollinger-Ellison syndrome (Stadil, ibid., pp 729–739), and some colorectal tumors may also be gastrin/CCK dependent (Singh, Walker, Townsend and Thompson, Cancer Research 46:1612, 1986, and Smith, J. P., Gastroenterology 95:1541, 1988). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxyl-terminus fragments of this peptide (e.g., the octapeptide CCK26-33 and the tetrapeptide CCK30-33). (G. J. Dockray, Br. Med. Bull. 38(3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. ("Cholecystokinin: Isolation, Structure and Functions," G. B. J. Glass, Ed., Raven Press, New York, 1980, pp 169–221; J. E. Morley, Life Sciences 27:355–368, 1980; "Cholecystokinin in the Nervous System," J. de Belleroche and G. J. Dockray, Ed., Ellis Horwood, Chichester, England, 1984, pp 110–127.)

The high concentrations of CCK peptides in many brain areas also indicate major brain functions for these peptides (G. J. Dockray, Br. Med. Bull. 38(3):253–258, 1982). The most abundant form of brain CCK found is CCK26-33, although small quantities of CCK30-33 exist (Reheld and Gotterman, J. Neurochem. 32: 1339–1341, 1979). The role of central nervous system CCK is not known with certainty, but it has been implicated in the control of feeding (Dalla-Fera and Baile, Science 206:471–473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al, J. Neuroscience 8:988–1000, 1988). Agents that modify GABA action may have utility as anxiolytic or hypnotic agents (S. C. Harvey, The Pharmacological Basis of Therapeutics (7th ed.) 1985, pp 399–371, MacMillan). Thus, agents which modify CCK action may have parallel anxiolytic or hypnotic activities. Aminoacyl-glycolic and -lactic esters are known as pro-drugs of amino acids (C. G. Wermuth, Chemistry and Industry, 433–435, 1980). Pro-drugs and soft drugs are known in the art (E. Palomino, Drugs of the Future 15(4) 361–368, 1990). The last two citations are hereby incorporated by reference.

The role of CCK in anxiety is disclosed in TIPS 11:271–273, 1990). Stella, V. J., et al, "Prodrugs", Drug Delivery Systems, pp. 112–176, 1985 and Drugs 29:455–73, 1985 disclose the concept of pro-drugs. J. Med. Chem. 33:344–347, 1990, disclosed pro-drug half esters. None of the foregoing references discloses pro-drugs of CCK antagonists.

SUMMARY OF THE INVENTION

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a pro-drug form.

A pro-drug is a drug which has been chemically modified and may be biologically inactive at its site of action, but which may be degraded or modified by one or more enzymatic or other in vivo processes to the parent bioactive form.

This chemically modified drug, or pro-drug, should have a different pharmacokinetic profile to the parent, enabling easier absorption across the mucosal epithelium, better salt formulation and/or solubility, improved systemic stability (for an increase in plasma half-life, for example). These chemical modifications may be 1) ester or amide derivatives which may be cleaved by esterases or lipases, for example, 2) peptides which may be recognized by specific or nonspecific proteinases, 3) derivatives that accumulate at a site of action through membrane selection of a pro-drug form or modified prodrug form, or any combination of 1 to 3 above.

Current research in animal experiments has shown that the oral absorption of certain drugs may be increased by the preparation of "soft" quaternary salts. The quaternary salt is termed a "soft" quaternary salt since, unlike normal quaternary salts, e.g., $R\text{---}N^+(CH_3)_3$, it can release the active drug on hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micellese and unionized ion pairs with bile acids, etc., which are able to penetrate the intestinal epithelium more effectively. The pro-drug, after absorption, is rapidly hydroxylzed with release of the active parent drug.

The invention relates to novel compounds which are pro-drugs of the formula

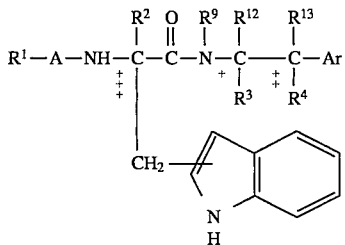

and the pharmaceutically acceptable salts thereof wherein $R^1$, $R^2$, $R^3$, $R^4$, $R^9$, $R^{12}$, $R^{13}$, A and Ar are as defined hereinbelow. Commonly owned copending applications 07/576,308, 07/576,628, 07/576,296, 07/576,024, 07/576,297, filed on Aug. 31, 1990, by Horwell, et al, the disclosures in which are herein incorporated by reference, disclose CCK antagonists.

In the continuation-in-part applications of the above applications also commonly owned and copending 07/726,656, 07/726,655, 07/726,654, 07/726,652, and 07/726,651, filed on even date herewith by Horwell, et al, the disclosures of which are incorporated herein by reference, CCK antagonists are disclosed.

The invention also relates to a pharmaceutical composition containing an effective amount of a compound according to formula I in combination with a pharmaceutically acceptable carrier in unit dosage form effective for appetite suspension.

The compounds are also useful as anxiolytics, antipsychotics, especially for treating schizophrenic behavior, as agents in treating disorders of the extraphyramidal motor system, as agents for blocking the trophic and growth stimulating actions of CCK and gastrin, and as agents for treating gastrointestinal motility.

Compounds of the invention are also useful as analgesics and potentiate the effect of morphine. They can be used as an adjunct to morphine and other opioids in the treatment of severe pain such as cancer pain and reduce the dose of morphine in treatment of pain where morphine is contraindicated.

An additional use for compounds such as the iodinated compound of Example 6 is that the suitable radiolabeled derivative such as iodine-131 or iodine-127 isotope gives an agent suitable for treatment of gastrin dependent tumors such as those found in colonic cancers. I-125 radiolabelled compound of Example 6 can also be used as a diagnostic agent by localization of gastrin and CCK-B receptors in both peripheral and central tissue.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing an effective amount of a compound of formula I in combination with a pharmaceutically acceptable carrier in unit dosage form effective for reducing gastric acid secretion.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of formula I in combination with a pharmaceutically acceptable carrier in unit dosage form effective for treating psychosis, i.e., schizophrenia.

The invention further relates to a method for treating psychosis in mammals which comprises administering an amount effective for treating psychoses of a composition as described above to a mammal in need of such treatment.

The invention also relates to a pharmaceutical compositions effective for stimulating or blocking CCK or gastrin receptors, for altering the activity of brain neurons, for schizophrenia, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, caffeine, opioids, alcohol, and nicotine. Withdrawal symptoms are treated by administration of an effective withdrawal treating amount of a compound of the instant invention.

The invention also relates to a pharmaceutical composition containing an effective amount of a compound of formula I in combination with a pharmaceutically acceptable carrier in unit dosage form effective for treating and/or preventing panic.

The invention also relates to a method for treating and/or preventing panic in mammals which comprises administering an amount effective for panic treatment and/or prevention of the composition described above to a mammal in need of such treatment.

The invention further relates to the use of the compounds of formula I to prepare pharmaceutical and diagnostic compositions for the treatment and diagnosis of the conditions described above.

The invention further provides processes for the preparation of compounds of formula I.

The invention further provides novel intermediates useful in the preparation of compounds of formula I and also provides processes for the preparation of the intermediates.

DETAILED DESCRIPTION

The compounds of the present invention are pro-drugs of compounds of formula I which are formed by the condensation of two modified amino acids and are therefore not peptides. Rather they are "dipeptoids", synthetic peptide-related compounds differing from natural dipeptides in that the substituent group $R^2$ is not commonly over hydrogen. The compounds are disclosed in copending commonly owned U.S. Ser. No. 545,222, filed Jun. 28, 1990, the disclosure of which is hereby incorporated by reference.

The compounds of the present invention are represented by the formula

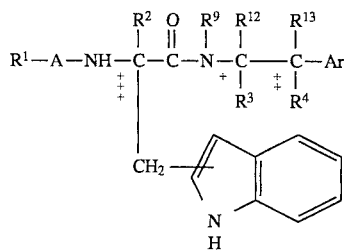

or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and $—(CH_2)_nOR^5$ wherein R* is hydrogen, straight or branched alkyl of from one to six carbon atoms, $—(CH_2)_nAr$, —COAr, $—(CH_2)_nOCOAr$, or $—(CH_2)_nNR^5COAr$ and R* may also independently be R as defined below, and R must be present at least once in formula I and R** is attached to formula I through a metabolically labile bond and can include

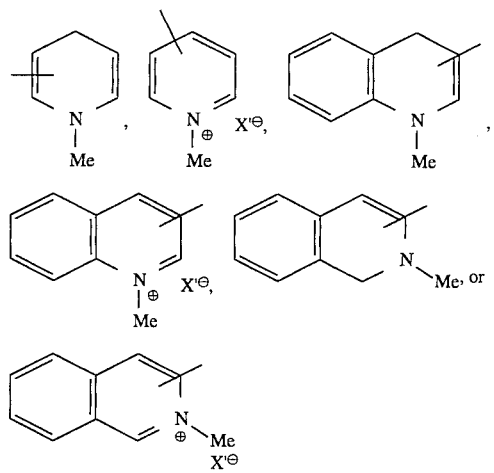

$R^5$ and $R^6$ are each independently hydrogen or alkyl of from one to about six carbon atoms and n is an integer from zero to six;

and R** is $—(CH_2)_nNR^5R^6$, $—(CH_2)_n—B—D^*$ wherein D* is O—COR*, $CO_2Ar^2$, $(CH_2)_nAr^2$, $OCOAr^2$, $NR^5COAr^2$, $COAr^2$, $CO_2CH(R)—CO_2R^*$, $CO_2—(CH_2)_nOCOR^*$ where $Ar^2$ is independently taken from Ar and where m is as defined below, $CONHCH(R)CO_2R^*$ where R is a side chain of a biologically significant amino acid, R is hydrogen only when B is not a bond, $—CO_2CH_2CH_2N^+(R^*)_3X^{1-}$ when $X^{1-}$ is a pharmaceutically acceptable counter anion,

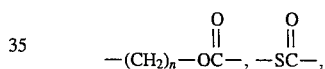

$—O—(CH_2)_nCO—$ or $—HC=CHCO—$ wherein n is an integer from zero to six;

$R^2$ is a straight or branched alkyl of from one to about six carbon atoms, $—HC=CH_2$, $—≡CH$, $—(CH_2)_n—CH=CH_2$, $—(CH_2)_nC≡CH$, $—(CH_2)_nAr$, $—(CH_2)_nOR^*$, $—(CH_2)_nOAr$, $—(CH_2)_nCO_2R^*$, or $—(CH_2)_nNR^5R^6$ wherein n, R*, $R^5$ and $R^6$ are as defined above and Ar is as defined below;

$R^3$ and $R^4$ are each independently selected from hydrogen, $R^2$ and $—(CH_2)_n—B—D$ wherein:

n' is an integer of from zero to three;

B is a bond,
$—OCO(CH_2)_n—$,
$—O(CH_2)_n—$,
$—NHCO(CH_2)_n—$,
$—CONH(CH_2)_n—$,
$—NHCOCH=CH—$,
$—COO(CH_2)_n—$,
$—CO(CH_2)_n—$,
$—S—(CH_2)_n—$,
$—S(=O)—(CH_2)_n—$,
$—SO_2—(CH_2)_n—$,
$—NHSO_2—(CH_2)_n—$,
$—SO_2NH—(CH_2)_n—$,

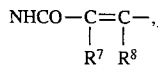

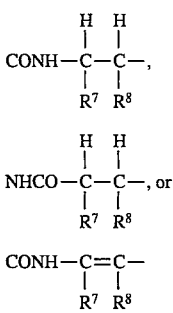

wherein $R^7$ and $R^8$ are each independently selected from hydrogen and $R^2$ or together form a ring $(CH_2)_m$ wherein m is an integer of from 1 to 5 and n is as defined above;

D is hydrogen,
—COOR*,
—CH$_2$NR$^5$R*,
—CHR$^2$NR$^5$R*,
—CH$_2$OR*,
CHR$^2$OR*,
CH$_2$SR*,
CHR$^2$SR*,
CONR$^5$R$^6$,
CONR$^5$R*, an acid replacement selected from

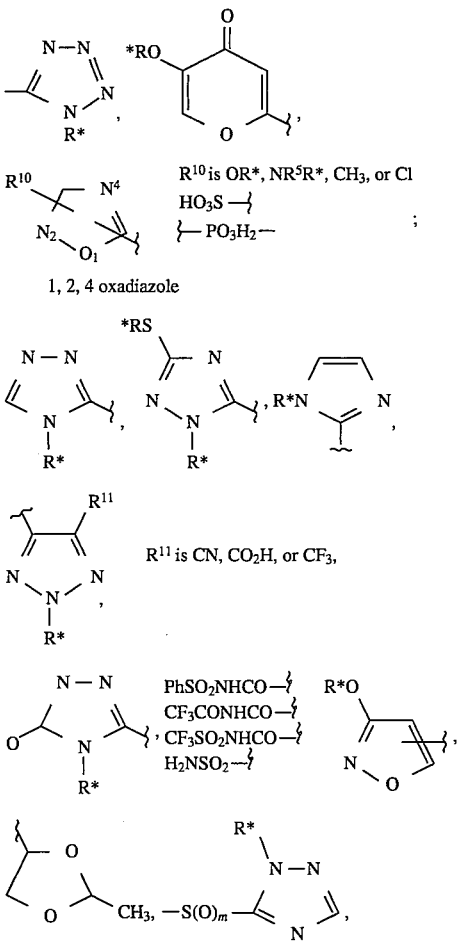

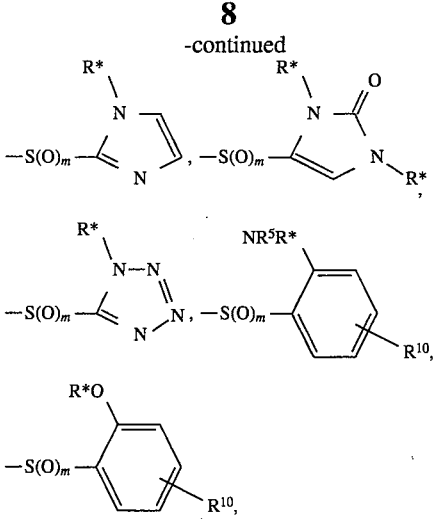

wherein m is an integer of from 0 to 2
wherein R*, $R^2$, $R^5$, and $R^6$ are as defined above;

$R^9$ is hydrogen or a straight or branched alkyl of from one to about six carbon atoms, —(CH$_2$)$_n$CO$_2$R*, —(CH$_2$)$_n$NR$^5$R*, wherein n, R*, and $R^5$ are as defined above or taken from $R^3$;

$R^{12}$ and $R^{13}$ are each independently hydrogen or are each independently taken with $R^3$ and $R^4$, respectively, to form a moiety doubly bonded to the carbon atom; and Ar is a mono- or polycyclic unsubstituted or substituted carbo- or heteroaromatic or carbo- or heterohydroaromatic moiety.

Preferred Ar is 2- or 3-thienyl, 2- or 3-furanyl, 2-, 3-, or 4-pyridinyl or an unsubstituted or substituted benzene ring

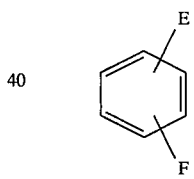

wherein E and F are each independently $R^3$ as defined above, hydrogen, fluorine, chlorine, bromine, iodine, methyl, methoxy, trifluoromethyl, or nitro.

Especially preferred Ar is from $R^3$ as defined as the ortho (2-) position of the ring, for example,

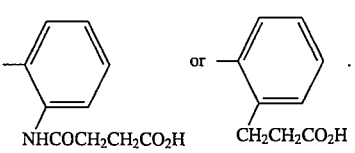

Preferred cycloalkyl or polycycloalkyl substituents have from six to ten carbon atoms.

Preferred compounds of the instant invention are those wherein cycloalkyl or polycycloalkyl is independently R*, F, Cl, Br, OR*, NR$^5$R*, CF$_3$, SR*.

Other preferred compounds of the instant invention are those wherein polycycloalkyl is selected from the group consisting of

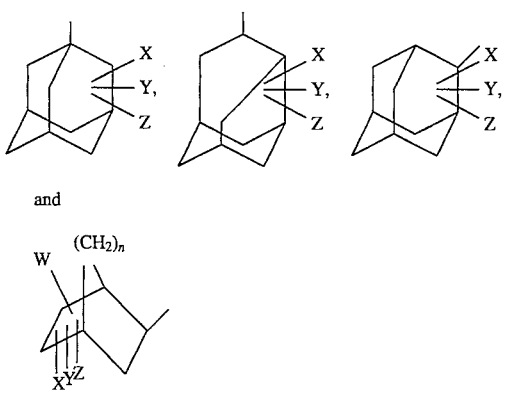

and wherein W, X, Y, and Z are each independently hydrogen, a straight or branched alkyl of from one to six carbon atoms, $CF_3$, $NR^5R^6$, $—(CH_2)_nCO_2R^*$, CN, F, Cl, Br, $OR^*$, $SR^*$, wherein $R^*$, $R^5$ and $R^6$ are as defined in claim 1 and n is an integer of from 1 to 3.

Other preferred compounds of the instant invention are those wherein $R^1$ is 2-adamantyl or 1-(S)-2-endobornyl;

A is —NHCO—, —OCO—, —$SO_2$—, —S(=O)— or —$CH_2CO$—;

$R^2$ is —$CH_3$, —$CH_2D^*$ or —$CH_2C≡CH$;

$R^3$ is —$(CH_2)_n$—B—D or H;

$R^4$ is —$(CH_2)_n$—B—D or H; and $R^9$ is hydrogen or methyl.

More preferred compounds of the instant invention are those wherein $R^1$ is 2-adamantyl or 1-(S)-2-endobornyl,

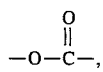

$R^2$ is —$CH_3$;

$R^3$ is H, —$CH_2OH$, —$CH_2OCOCH_2CH_2D^*$, —$CH_2SCH_2CH_2D^*$, —$CH_2SCH_2D$, —$CH_2D^*$, —$CH_2OCOCH=CHD^*$ or —$CH_2NHCOCH_2CH_2D^*$, or —$CH_2NHCOCH=CHD^*$ and $R^4$ is H, —$NHCOCH_2CH_2D^*$ ([D] configuration or —NHCOCH=CHD* ([D] configuration).

The D and the L configurations are possible at the chiral centers and are included in the scope of the invention:

1. Preferred is when $R^2$ is —$CH_3$[D] configuration;
2. Preferred is when $R^3$ is —$CH_2OCOCH_2CH_2D^*$ or —$CH_2NHCOCH_2CH_2D^*$ with the [D] configuration at the Trp ∝-carbon atom and the [L] configuration at the Phe-∝-carbon atom; and
3. Preferred is when $R^4$ is —$NHCOCH_2CH_2D^*$[D] configuration or NHCOCH=CHD*[D] configuration with the [D] configuration at the Trp ∝-carbon atom.

Preferred compounds of the instant invention are pro-drugs of the following:

[1S-[1∝,2β[S*[S*(E)]],4∝]]-4-[[2-[[3-(1 H-indol-3-yl)-2-methyl-1-oxo-2-[[[(1,7,7-trimethylbicyclo-[2.2.1] hept-2-yl)oxy]carbonyl]amino]propyl]amino]-1 -phenylethyl]amino]-4-oxo-2-butenoic acid,

[1S-[1∝,2β[S*(S*)], 4∝]]-4-[[2-[[3-(1H-indol-3 -yl)-2-methyl-1-oxo-2-[[[(1,7,7-trimethylbicyclo-[2.2.1]hept-2-yl)oxy]carbonyl]amino]propyl]methyl-amino]-1-phenyl-ethyl]amino]-4-oxobutanoic acid,

[1S-[1∝,2β[S*(S*)], 4∝]]-4-[[2 -[[3-(1H-indol-3-yl)-2-methyl-1-oxo-2-[[[(1,7,7-trimethylbicyclo-[2.2.1]hept-2-yl)amino]carbonyl]amino]propyl]amino]-1 -phenylethyl]amino]-4-oxobutanoic acid,

[R-(R*,R*)]-4-[[2-[[3-(1H-indol-3yl)-2-methyl-1 -oxo-2-[(tricyclo[3.3.1.1³,⁷]dec-2-ylsulfonyl)amino]-propyl]amino] -1-phenylethyl]amino]-4-oxobutanoic acid,

[R-(R*,S*)]-4-[[2-[[3-(1H-indol-3-yl)-2-methyl-1 -oxo-2-[(tricyclo[3.3.1.1³,⁷]dec-2-ylsulfonyl)amino]-propyl-amino]-3-phenylpropyl]amino]-4-oxobutanoic acid,

[1R-[1∝[R*(S*)],2β]] and [1S-[1∝[S*(R*)],2β]]-4-[[2-[[2-[[[(2-fluorocyclohexyl)oxy]carbonyl]amino]-3 -(1H-indol-3-yl)-2-methyl-1-oxopropyl]amino]-3 -phenylpropyl]amino]-4-oxobutanoic acid,

[1R-[1∝[R*(S*)], 2β]] and [1S-[1∝[S*(R*)],2β]]-4-[[2-[[2-[[[(2-fluorocyclohexyl)oxy]carbonyl]amino]-3 -(1H-indol-3-yl)-2-methyl-1-oxopropyl]methylamino]-3 -phenylpropyl]amino]-4-oxobutanoic acid,

[1R-[1∝[R*(S*)],2β]] and [1S-[1∝[S*(R*)],2β]]-4 -[[2-[[3-(1H-indol-3-yl)-2-methyl-1-oxo-2-[[[2-(trifluoromethyl)cyclohexyl]oxy]carbonyl]amino]propyl]-amino]-3-phenylpropyl]-amino]-4-oxobutanoic acid,

[1R-[1∝[R*(S*)],2β]] and [1S-[1∝[S*(R*)],2β]]-4 -[[2-[[3-(1H-indol-3-yl)-2-methyl-1-oxo-2-[[[2 -(trifluoromethyl)-cyclohexyl]oxy]carbonyl]amino]-propyl]methylamino]-3-phenylpropyl]amino]-4 -oxobutanoic acid,

[R-(R*,S*)]-4-[[2-[[3-(1H-indol-3-yl)-2-methyl-1 -oxo-2-[[(tricyclo[3.3.1.1³,⁷]dec-2-yloxy)carbonyl]-aminopropyl]methylamino]-3-phenylpropyl]amino]-4-oxobutanoic acid,

[1S-[1∝,2β[S*(R*)],4∝]]-[1-(1H-indol-3-ylmethyl)-1 -methyl-2-oxo-2-[[2-[[2-[[1-oxo-3-(1H-tetrazol-5 -yl)propyl]amino]-1-(phenylmethyl)ethyl]amino]ethyl]-carbamic acid, 1,7,7-trimethylbicyclo[2.2.1]hept-2-yl ester,

[1S-[1∝,2β[S*(R*)],4∝[[-[-(1H-indol-3-ylmethyl)-1 -methyl-2-oxo-2-[[2-[[1-oxo-3-(1H-tetrazol-5-yl)-propyl] amino]-2-phenylethyl]amino]ethyl]carbamic acid, 1,7,7-trimethyl-bicyclo[2.2.1]hept-2-yl ester, N-[2-methyl-N-[(tricyclo[3.3.1.1³,⁷]dec-2-yloxy)-carbonyl]-D-tryptophyl]-L-phenylalanylglycine, N-[2-methyl-N-[(tricyclo[3.3.1.1³,⁷]dec-2-yloxy)-carbonyl]-D-tryptophyl]-L-phenylalanyl-β-alanine.

In addition preferred compounds of the instant invention are pro-drugs of:

2-methylcyclohexyl [2-[[1-(hydroxymethyl)-2 -phenylethyl]amino]-1-(1H-indol-3-ylmethyl)-1-methyl-2 -oxoethyl]carbamate, 2-[[2-[[[(2-chlorocyclohexyl)oxy]carbonyl]amino]-3-(1H-indol-3-yl)-2-methyl-1-oxopropyl]amino]-3 -phenylpropyl butanedioate, 2-[[2-[[[(2-methylcyclohexyl)oxy]carbonyl]amino]-3 -(1H-indol-3-yl)-2-methyl-1-oxopropyl]amino]-3 -phenylpropyl butanedioate, tricyclo[3.3.1.1³,⁷]dec-2-yl [2-[[1 -(hydroxymethyl)-2-phenylethyl]amino]-1-(1H-indol-3-yl-methyl)-1 -methyl-2-oxoethyl] carbamate, 2-[[3-(1H-indol-3-yl)-2-methyl-1-oxo-2 -[[(tricyclo[3.3.1.1³,⁷]dec-2-yloxy)carbonyl]amino]-propyl]amino]-3-phenylpropyl butanedioate, 2-[[3-(1H-indol-3-yl)-2-methyl-1-oxo-2 -[[(tricyclo[3.3.1.1³,⁷]dec-2-yloxy)carbonyl]amino]-propyl]amino]-1-phenylethyl butanedioate,

[R-(R*,R*)]-4-[[2-[[3-(1H-indol-3-yl)-2-methyl-1 -oxo-2-[[(tricyclo[3.3.1.1³,⁷]dec-2-yloxy)carbonyl]-aminopropyl]amino]-1-phenylethyl]amino]-4-oxobutanoic acid,

[1S-[1∝,2β[S*(S*)],4∝]]-4-[[2-[[3-(1H-indol-3 -yl)-2-methyl-1-oxo-2-[[[(1,7,7-trimethylbicyclo-2.2.1]hept-2

-yl)oxy]carbonyl]amino]propyl]amino]-1 -phenylethyl] amino]-4-oxobutanoic acid,

[R-[R*,S*-(E)]]-4-[[2-[[3-(1H-indol-3-yl)-2 -methyl-1-oxo-2-[[tricyclo[3.3.1.1$^{3,7}$]dec-2 -yloxy) carbonyl]amino] propyl]amino]-3-phenylpropyl]amino]-4-oxo-2-butenoic acid, 8 R-(R*,S*)]-4-[[2-[[3-(1H-indol-3-yl)-2-methyl-1 -oxo-2-[[(tricyclo[3.3.1.1$^{3,7}$]dec-2-yloxy)carbonyl]-amino]propyl]amino]-3-phenylpropyl]amino]-4-oxobutanoic acid, (R)-tricyclo[3.3.1.1$^{3,7}$]dec-2-yl [1-(1H-indol-3 -ylmethyl)-1-methyl-2-[methyl(2-phenylethyl)amino]-2-oxoethylcarbamate,

[R-(R*,S*)]-[[2-[[3-(1H-indol-3-yl)-2-methyl-1 -oxo-2-[[(tricyclo[3.3.1.1$^{3,7}$]dec-2-yloxy)]carbonyl]-amino]propyl] amino]-3-phenylpropyl]sulfinyl]-acetic acid, ethyl ester,

[R-(R*,S*)]-[[2-[[3-1H-indol-3-yl)-2-methyl-1 -oxo-2-[[(tricyclo[3.3.1.1$^{3,7}$]dec-2-yloxy)]carbonyl]-amino]propyl] amino]-3-phenylpropyl]sulfonyl]-acetic acid, ethyl ester,

[R-(R*,S*)]-[[2-[[3-(1H-indol-3-yl)-2-methyl-1 -oxo-2-[[(tricyclo[3.3.1.1$^{3,7}$]dec-2-yloxy)]carbonyl]-amino]propyl] amino]-3-phenylpropyl]sulfinyl]-acetic acid,

[R-[R*,R*-(E)]]-4-[[2-[[3-(1H-indol-3-yl)-2 -methyl-1-oxo-2-[[(tricyclo[3.3.1.1$^{3,7}$]dec-2-yloxy)]carbonyl]amino] propyl]amino]-1 -phenylethyl]amino]-4-oxo-2-butenoic acid,

[R-(R*,S*)]-[[2-[[2-[3-(1H-indol-3-yl)-2-methyl-1 -oxo-2-[[(tricyclo[3.3.1.1$^{3,7}$]dec-2-yloxy)]carbonyl]-amino]propyl]amino]-3-phenylpropyl]thio]acetic acid,

[1S-[1∝,2β[S*[S*(E)]],4∝]]-4-[[2-[[3-(1H-indol-3 -yl)-2-methyl-1-oxo-2-[[[(1,7,7-trimethylbicyclo-[2.2.1]hept-2-yl)oxy]carbonyl]amino]propyl]amino]-1-phenylethyl] amino]-4-oxo-2-butenoic acid, methyl ester, (Bicyclo system is 1S-endo),

[1S-[1∝,2β[S*[S*(E)]],4-[[2-[[3-(1H-indol-3 -yl)-2-methyl-1-oxo-2-[[[(1,7,7-trimethylbicyclo-[2.2.1]hept-2-yl)oxy]carbonyl]amino]propyl]amino]-1 -phenylethyl] amino]-4-oxo-2-butenoic acid, (Bicyclo system is 1S-endo),

[R-(R*,R*)]-3-[[2-[[3-(1H-indol-3-yl)-2-methyl-1 -oxo-2-[[(tricyclo[3.3.1.1$^{3,7}$]dec-2-yloxy)]carbonyl] -amino]propyl]amino]-1-phenylethyl]amino]-3-oxo-propanoic acid,

[R-(R*,S*)]-3-(1H-indol-3-ylmethyl)-3-methyl-4,10 -dioxo-6-(phenylmethyl)-11-oxo-8-thia-2,5 -diazatridecanoic acid, tricyclo [3.3.1.1$^{3,7}$]dec-2-yl or ester,

[R-(R*,S*)]-β-[[3-(1H-indol-3-yl)-2-methyl-1-oxo-2 -[[(tricyclo[3.3.1.1$^{3,7}$]dec-2-yloxy)]carbonyl]amino]-propyl]amino]benzenebutanoic acid,

[R-(R*,S*)]-N-[3-[[3-(1H-indol-3-yl)-2-methyl-1 -oxo-2-[[(tricyclo[3.3.1.1$^{3,7}$]dec-2-yloxy)]carbonyl]-amino]propyl]amino]-4-phenylbutyl]glycine,

[R-[R*,S*-(E)]]-4-[[2-[[3-(1H-indol-3-yl)-2 -methyl-2-[[(bicyclo[3.3.1]non-9-yloxy)carbonyl]amino]-1-oxopropyl] -amino]-3-phenylpropyl]amino]-4-oxo-2 -butenoic acid, mono [R-(R*,R*)]-2-[[3-(1H-indol-3-yl)-2-methyl-1 -oxo-2-[[(tricyclo[3.3.1.1$^{3,7}$]dec-2-yloxy)carbonyl]-amino]-1-phenylethyl butanedioate, 3-[[3-[[3-(1H-indol-3-yl)-2-methyl-1-oxo-2 -[[(tricyclo-[3.3.1.1$^{3,7}$]dec-2-yloxy)]carbonyl]-amino]propyl]amino]-1-oxo-2-phenylpropyl]amino]-propanoic acid (TRP is R, other center is RS),

[1R-[1∝[R*(S*)],2β]]-4-[[2-[[3-(1H-indol-3-yl)-2 -methyl-2-[[[(2-methyl-1-cyclohexyl)oxy]carbonyl]-amino]-1-oxopropyl]-amino]-3-phenylpropyl]amino]-4 -oxo-2-butenoic acid, (−)-Isomer,

[1R-[1∝[R*(S*)],2β]]-4-[[2-[[3-(1H-indol-3 -yl)-2-methyl-2-[[[(2-methyl-1-cyclohexyl)oxy]carbonyl]-amino]-1-oxopropyl]-amino]-3-phenylpropyl]amino]-4 -oxobutanoic acid, (−)-Isomer,

[1R-[1∝[R*(S*)],2β]]-4-[[2-[[3-(1H-indol-3-yl)-2 -methyl-2-[[[(2-methyl-1-cyclohexyl)oxy]carbonyl]-amino]-1-oxopropyl]-amino]-1-phenylethyl]amino]-4-oxo-2 -butenoic acid, (−)-Isomer,

[1R-[1∝[R*(S*)],2β]]-4-[[2-[[3-(1H-indol-3-yl)-2 -methyl-2-[[[(2-methyl-1-cyclohexyl)oxy]carbonyl]-amino]-1 -oxopropyl]-amino]-1-phenylethyl]amino]-4 -oxobutanoic acid, (3I)-Isomer, 2-methylcyclohexyl-[1R-[1∝[R*(S*)]],2β]-[2-[[1 -(hydroxymethyl)-2-phenylethyl]amino]-1-(1H-indol-3-ylmethyl)-1 -methyl-2-oxoethyl]carbamate,

[R-[R*,S*-(E,E)]]-6-[[3-(1H-indol-3-yl)-2-methyl-1 -oxo-2-[[(tricyclo-[3.3.1.1$^{3,7}$]dec-2-yloxy)carbonyl]amino] propyl]-amino]-7-phenyl-2,4-heptadienoic acid,

[R-(R*,R*)]-[2-[[2-[[1,4-dioxo-4-(1H-tetrazol-5 -ylamino)-butyl]amino]-2-phenylethyl]amino]-1-(1H-indol-3 -ylmethyl)-1-methyl-2-oxoethyl]carbamic acid, tricyclo-[3.3.1.1$^{3,7}$]dec-2-yl-[S-[R*,S*-(E)]]-12 -(1H-indol-3-ylmethyl)-12-methyl-3,11-dioxo-9-(phenylmethyl)-2 -oxa-7,10,13-triazatetradec-4-en-14-oate,

[R-(R*,S*)]-3-[[2-[[3-(1H-indol-3-yl)-2-methyl-1 -oxo-2-[[(tricyclo-[3.3.1.1$^{3,7}$]dec-2-yloxy)carbonyl]-amino]propyl]-amino]-3-phenylpropyl]amino]-3 -oxopropanoic acid, ethyl [R-(R*,S*)]-[[2-[[2-[3-(1H-indol-3-yl)-2 -methyl-1-oxo-2-[[(tricyclo[3.3.1.1$^{3,7}$]dec-2 -yloxy)carbonyl]amino] -propyl]amino]-3-phenylpropyl]-thio]acetate,

[R-(R*,S*)]-62 -[[3-(1H-indol-3-yl)-2-methyl-1-oxo-2 -[[tricyclo[3.3.1.1$^{3,7}$]dec-2-yloxy)carbonyl]amino-propyl] amino]-4-iodo-benzenebutanoic acid,

[R-(R*,R*)]-[2-[[3-(1H-indol-3-yl)-2-methyl-1 -oxo-2-[ [(1(tricyclo[[(3.3.1.1$^{3,7}$]dec-2-yloxy)carbonyl]-amino]-propyl]amino]-1-phenylethoxy]acetic acid,

[[3-[[3-(1H-indol-3-yl)-2-methyl-1-oxo-2 -[[tricyclo(3.3.1.1$^{3,7}$]dec-2-yloxy)carbonyl]amino] -propyl]amino] -1-oxo-2-phenylpropyl]amino]acetic acid (TRP center is R, other center is RS), (R)-[[[2-[[3-(1H-indol-3-yl)-1-oxo-2-methyl-2 -[[(tricyclo[3.3.1.1$^{3,7}$]dec-2-yloxy)carbonyl]amino]-propyl] amino]-1-phenylethylidene]amino]oxy]acetic acid,

[R-(R*,S*)]-β-[[3-(1H-indol-3-yl)-2-methyl-1-oxo-2 -[[(tricyclo[3.3.1.1$^{3,7}$]dec-2-yloxy)carbonyl]amino]-propyl] -amino]benzenebutanoic acid,

[R-(R*,S*)]-N-[3-[[3-(1H-indol-3-yl)-2-methyl-1 -oxo-2-[[(tricyclo-[3.3.1.1$^{3,7}$]dec-2-yloxy)carbonyl]-propyl] amino]-4-phenylbutyl]glycine, 2-[[[2-[[3-(1H-indol-3-yl)-2-methyl-1-oxo-2 -[[(tricyclo-[3.3.1.1$^{3,7}$]dec-2-yloxy)carbonyl]-amino]propyl]amino]-1-phenylethyl]amino]carbonyl]-cyclopropanecarboxylic acid (cyclopropane ring is trans-(±) other centers are R), carbamic acid, [1-(1H-indol-3-ylmethyl)-1-methyl-2 -oxo-2-[[2-[[1-oxo-3-(1H-tetrazol-5-yl)propyl]amino]-2-phenylethyl]-amino]ethyl]-,tricyclo[3.3.1.1$^{3,7}$]dec-2 -yl ester,[R, (R*,S*]-, benzeneheptanoic acid, ∝-[[3-(1H-indol-3-yl)-2 -methyl-1-oxo-2-[[(tricyclo[3.3.1.1$^{3,7}$]dec-2 -yloxy)carbonyl]amino] -propyl]amino]-,[R-(R*,S*)]-, methyl-(±)-β-[[(2-phenylethyl)amino]carbonyl]-1β-[ [(tricyclo[3.3.1.1$^{3,7}$]dec-2-yloxy)carbonyl]amino]-1H -indole-3-butanoate,

[R-(R*,S*)]-4-[[2-(1H-indol-3-yl)-2-methyl-1-oxo-2 -[[tricyclo[3.3.1.1$^{3,7}$]dec-2-yloxylcarbonyl]amino]-propyl] -amino]-3-phenylpropyl]amino]-4-oxo-2-butenoic acid, bicyclo[2.2.1]heptane-2-acetic acid, 3-[[[[2-[[1 -(hydroxymethyl)-2-phenylethyl]amino]-1-(1H-indol-3 -ylmethyl)-1-methyl-2-oxoethyl]amino]carbonyl]oxy]-4,7,7 -trimethyl-,[1R-[1∝,2β,3∝[R*(S*)],4∝]]-, butanoic acid, 4-[[2-[[3-(1H-indol-3-yl)-2-methyl-2-[[ [(2-methyl-1-cyclohexyl)oxy]carbonyl]-amino]-1-oxopropyl]-amino]-1-phenylethyl]amino]-4-oxo-[1R-[1∝[R*(R*)]
2β]]-((−)-isomer, 2-butenoic acid, 4-[[2-[[3-(1H-indol-3-yl)-2-methyl-2-[[
[)2-methyl-1-cyclohexyl)oxy]carbonyl]-amino]-1-oxopropyl]-amino]-1-phenylethyl]amino]-4-oxo-,[1R-[1∝[R*(R*)]],2β]]-((−)-isomer), butanoic acid, 4-[[2-[[3-(1H-indol-3-yl)-2-methyl-2-[[
[)2-methyl-1-cyclohexyl)oxy]carbonyl]-amino]-1-oxopropyl]-amino]-3-phenylpropyl]amino]-4-oxo-[1R-[1∝[R*(S*)]],2β]]-((−)-isomer), and 2-butenoic acid, 4-[[2-[[3-)1H-indol-3-yl)-2-methyl-2-[[
[(2-methyl-1-cyclohexyl)oxy]carbonyl]-amino]-1-oxopropyl]-amino]-3-phenylpropyl]amino]-4-oxo-[IR[1∝[R*(S*)],2β]]-((−)-isomer).

Additionally preferred are the pro-drugs of the compounds:

[[3-[[3-(1H-indol-3-yl)-2-methyl-1-oxo-2-[[tricyclo[3.3.1.1$^{3,7}$]-dec-2-yloxy)carbonyl]amino]-propyl]amino]-1-oxo-2-phenylpropyl]-amino]acetic acid, (TRP center is R, other center is RS),

[R-(R*,R*)]-2-[[3-(1H-indol-3-yl)-2-methyl-1-oxo-2-[[tricyclo[3.3.1.1$^{3,7}$]dec-yloxy)carbonyl]-amino]-propyl]amino]-1-phenylethoxy]acetic acid,

[1R-[1α,2β[R*(R*)]]]-2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]-amino]carbonyl]cyclopropane carboxylic acid,

[1S-[1α-2β[S*(S*)]]]-2-[[[2-[[3-(1H-indol-3-yl)-2-methyl-1-oxo-2-[[(tricyclo[3.3.1.1$^{3,7}$]dec-2-yloxy)carbonylamino]propyl]amino]-1-phenylethyl]-amino]carbonylcyclopropane carboxylic acid,

[R-R*,R*)]-3-[2-[[3-(1H-indol-3-yl)-2-methyl-1-oxo-2-[[(tricyclo[3.3.1.1$^{3,7}$]dec-2-yloxy)carbonyl]-amino]propyl]amino]-1-phenylethoxy]propanoic acid,

[R-R*,R*)]-mono2-[[3-(1H-indol-3-yl)-2-methyl-1-oxo-2-[[(tricyclo[3.3.1.1$^{3,7}$]dec-2-yloxy)carbonyl]-amino]-1-phenylethyl butanedioic acid, 3-[[3-[[3-(1H-indol-3-yl)-2-methyl-1-oxo-2-[[(tricyclo[3.3.1.1$^{3,7}$]dec-2-yloxy)carbonyl]amino]-propyl]amino]-1-oxo-2-phenylpropyl]amino]propanoic acid, (TRP is R, other center is RS,)

[R-(R*,S*)]-β-[[3-(1H-indol-3-yl)-2-methyl-1-oxo-2-[[(tricyclo-[3.3.1.1$^{3,7}$]dec-2-yloxy)carbonyl]-amino]propyl]amino]-4-iodobenzenebutanoic acid,

[1R-1α[R*(S*)],2β]]-4-[[2-[[3-(1H-indol-3-yl)-2-methyl-2-[[[(2-methyl-1-cyclohexyl)oxy]carbonyl]-amino]-1-oxopropyl]amino]-3-phenyl-propyl]amino]-4-oxo-2-butenoic acid, ((−)-isomer),

[1R-[1α[R*,(S*)],2β]]-4-[[2-[[3-(1H-indol-3-yl)-2-methyl-2-[[[(2-methyl-1-cyclohexyl)oxy]carbonyl]-amino]-1-oxopropyl]amino]-3-phenylpropyl]amino]-4-oxobutanoic acid, ((−)-isomer),

[1R-1α[R*(R*)][,2β]]-4-[[2-[[3-(1H-indol-3-yl)-2-methyl-2-[[[(2-methyl-1-cyclohexyl)oxy]carbonyl]-amino]-1-oxopropyl]amino-1-phenylethyl]amino]-4-oxo-2-butenoic acid, ((−)-isomer), 1R-[2α[R*(R*)],2β]]-4-[[2-[[3-1H-indol-3-yl)-2-methyl-2-[[[(2-methyl-1-cyclohexyl)oxy]carbonyl]-amino]-1-oxopropyl]amino]-1-phenylethyl]amino]-4-oxobutanoic acid, ((−)-isomer),

[R-(R*,S*)]-1g-[[3-(1H-indol-3-yl)-2-methyl-1-oxo-2-[[(tricyclo[3.3.1.1$^{3,7}$]dec-2-yloxy)carbonyl]-amino]propyl]amino]-benzeneheptanoic acid, 2-[[2-[[3-(1H-indol-3-yl)-2-methyl-1-oxo-2-[[(tricyclo-[3.3.1.1$^{3,7}$]dec-2-yloxy)carbonyl]-amino]propyl]amino]-1-phenylethyl]amino]carbonyl]-cyclopropanecarboxylic acid, (cyclopropyl ring is trans-(±), other centers are R), 2-methylcyclohexyl[1R-[1α[R*(S*)]],2β]-[2-[[1-hydroxymethyl)-2-phenylethyl]amino]-1-(1H-indol-3-ylmethyl)-1-methyl-2-oxoethyl]-carbamate, ((−)-isomer),

[R-[R*,S*-(E,E)]]-6-[[3-(1H-indol-3-yl)-2-methyl-1-oxo-2-[[(tricyclo[3.3.1.1$^{3,7}$]dec-2-yloxy)carbonyl]-amino]propyl]amino]-7-phenyl-2,4-heptadienoic acid, tricyclo[3.3.1.1$^{3,7}$]dec-2-yl[2-[[1[(hydroxymethyl)-2-hydroxy-2-phenylethyl]amino]-1-(1H-indol-3-ylmethyl)-1-methylethyl]carbamate, tricyclo[3.3.1.1$^{3,7}$]dec-2-yl[R-(R*,R*)]-[1H-indol-3-ylmethyl)-1-methyl-2-oxo-2-[[2-[[1-oxo-3-(1H-tetrazol-5-yl)propyl]amino]-2-phenylethyl]amino]-ethyl]carbamate,

[R-(R*,S*)]-2-[[2-[[3-(1H-indol-3-yl)-2-methyl-1-oxo-2-[[(tricyclo[3.3.1.1$^{3,7}$]dec-2yloxy)carbonyl]-amino]propyl]amino]-3-phenylpropyl[sulfonyl]acetic acid,

[R-(R*,S*)]-[[2-[[3-(1H-indol-3-yl)-2-methyl-1-oxo-2-[[(tricyclo[3.3.1.1$^{3,7}$]dec-2-yloxy)]carbonyl]-amino]propyl]amino]-3-phenylpropyl[sulfonyl]acetic acid, Ethyl [R-(R*,S*)]-[[2-[[3-(1H-indol-3-yl)-2-methyl-1oxo-2-[[(tricyclo[3.3.1.1$^{3,7}$]dec-2-yloxy)]carbonyl]amino]propyl]amino]-3-phenylpropyl]-sulfonyl]acetate, 2-chlorocyclohexyl [2-[[1-(hydroxymethyl)-2-phenylethyl]amino]-1-(1H-indol-3-ylmethyl)-1-methyl-2-oxoethyl]carbamate, Isomer II, (ring centers are trans, trp center is D, other center is S), ((−) or (+) form),

[R-[R*,S*(E)]]-4-[[2-[[3-(1H-indol-3-yl)-2-methyl-1-oxo-2-[[)tricyclo[3.3.1.1$^{3,7}$]dec-2-ylamino)carbonyl]amino]propyl]amino]-1-phenylethyl]amino]-4-oxo-2-butenoic acid,

[R-(R*,R*)]-4-[[2-[[3-(1H-indol-3-yl)-2-methyl-1-oxo-2-[[(tricyclo[3.3.1.1$^{3,7}$ dec-2-yloxy)carbonyl]-amino]propyl]amino]-1-phenylethyl]amino]-4-oxobutanoic acid,

[R-(R*,S*)]-mono[2-[[3-(1H-indol-3-yl)-2-methyl-1-oxo-2[[(tricyclo[3.3.1.1$^{3,7}$]dec-2-yloxy)carbonyl]-amino]propyl]amino]-3-phenylpropyl]butanedioate, tricyclo[3.3.1.1$^{3,7}$]dec-2-yl [R-(R*,S*)-[2-[[1-(hydroxymethyl)-2-phenylethyl]amino]-1-(1H-indol-3-ylmethyl)-1-methyl-2-oxoethyl]-carbamate,

[1S-[1α,2β[S*[S*(E)]],4α-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]amino]-1-phenylethyl]amino]-4-oxo-2-butenoic acid (bicyclo system is 1S-endo),

[1S-[1α,2β[S*(S*)],4α]]-4-[[2-[[3-(1H-indol-3-yl)-2-methyl-1-oxo-2-[[[(1,7,7-trimethylbicyclo-[2.2.1.1]hept-2-yl)oxy]carbonyl]-amino]propyl]amino]-1-phenylethyl]amino]-4-oxo-2-butenoic acid (bicyclo system is 1S-endo),

[R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]-amino]-4-oxo-2-butenoic acid, N-[2-methyl-N-[(tricyclo[3.3.1.1$^{3,7}$]dec-2-yloxy)carbonyl]-D-tryptophyl]-L-phenylalanylglycine,

[R-(R*,S*)]-4-[[2-[[3-(1H-indol-3-yl)-2-methyl-1-oxo-2-[[(tricyclo[3.3.1.1$^{3,7}$]dec-2-yloxy)carbonyl]-amino]propyl]amino]-3-phenylpropyl]amino]-4-oxobutanoic acid,

[R-(R*,R*)]-2-[[2-[[1,4-dioxo-4-(1H-tetrazol-5-ylamino)butyl]-amino]-2-phenylethyl]amino]-1-(1H-indol-3-ylmethyl)-1-methyl-2-oxoethyl]carbamic acid,

[R-(R*,R*)]-3-[[2-[[3-(1H-indol-3-yl)-2-methyl-1-oxo-2-[[(tricyclo[3.3.1.1$_{3,7}$]dec-2-yloxy)carbonyl]-amino]propyl]amino]-1-phenylethyl]amino]-3-oxo-propanoic acid,

[R-(R*,S*)]-3-[[2-[[3-(1H-indol-3-yl-2-methyl-1-oxo-2-[[(tricyclo[3.3.1.1$^{3,7}$]dec-2-yloxy)carbonyl]-amino]propyl]amino]-3-phenylpropyl]amino]-3-oxopropanoic acid,

[R-[R*,S*-(E)]]-4-8 [2-[[3-(1H-indol-3-yl)-2-methyl-2-[[(bicyclo[3.3.1.1]non-9-yloxy)carbonyl]-amino]-1-oxopropyl]amino]-3-phenylpropyl]amino]-4-oxo-2-butenoic acid,

[R-(R*,S*)]-5-[[2-[[3-(1H-indol-3yl)-2-methyl-1 -oxo-2-[[(tricyclo[3.3.1.1$^{3,7}$]dec-2-yloxy)carbonyl]-amino]propyl]amino]-3-phenylpropyl]amino]-5-oxopentenoic acid, Ethyl [R-(R*,S*)]-[[2-[[3-(1H-indol-3-yl)-2 -methyl-1-oxo-2-[[(tricyclo[3.3.1.1$^{3,7}$]dec-2 -yloxy)carbonyl]amino]propyl]amino]-3-phenylpropyl]-sulfinyl]acetate,

[R-[R*,R*-(E)]]-4-[[2-[[3-(1H-indol-3-yl)-2 -methyl-1-oxo-2-[[(tricyclo[3.3.1.1$^{3,7}$]dec-2 -yloxy)carbonyl]amino]propyl]amino]-1-phenylethyl]amino]4-oxo-2-butenoic acid,

[R-(R*,S*)]-N-[3-[[3-(1H-indol-3-yl)-2-methyl-1 -oxo-2-[[(tricyclo[3.3.1.1$^{3,7}$]dec-2-yloxy)carbonyl]-amino]propyl]amino]-1-oxo-4-phenylbutyl]-β-alanine, N-[N-[α-methyl-N-[(tricyclo[3.3.1.1$^{3,7}$]dec-2 -yloxy)carbonyl]-D-tryptophyl]-L-phenylalanyl]-L-alanine,

[R-R*,S*)]-3-[[2-[[3-1H-indol-3-yl)-2-methyl-1 -oxo-2-[[(tricyclo[3.3.1.1$^{3,7}$]dec-2-yloxy)carbonyl]-amino]propyl]aminoα-3-phenylpropyl]thio]propanoic acid,

[R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]-amino]propyl]amino]-3-phenylpropyl]thio]acetic acid,

[R-(R*,S*)]-β-[[3-(1H-indol-3-yl)-2-methyl-1-oxo-2-[[(tricyclo[3.3.1.1$^{3,7}$]dec-2-yloxy)carbonyl]-amino]propyl]amino]-benzenebutanoic acid, tricyclo[3.3.1.1$^{3,7}$]dec-2-yl[R-(R*,S*)]-3-(1H-indol-3-yl-methyl)-3-methyl-4,10-dioxo-6 -(phenylmethyl)-11-oxa-8-thia-2,5-diazatridcanoic acid, tricyclo[3.3.1.1$^{3,7}$]dec-2-yl 3-(1H-indol-3 -ylmethyl)-3,17,'7-trimethyl-4,9,12,16-tetraoxo-7-phenyl-13,15-dioxa-2,5,8-triazaoctadecanoate, 1-tricyclo[3.3.1.1$^{3,7}$]dec-2-yl 3-(1H-indol-3-ylmethyl)-3-methyl-4,9,12,16,-tetraoxo-7-phenyl-13,15 -dioxa-2,5,8-triazaeicosanediate, 1-tricyclo[3.3.1.1$^{3,7}$]dec-2-yl 3-(1H-indol-3 -ylmethyl)-3,17,17-trimethyl-4,9,12,16-tetraoxo-7-phenyl-13,15-dioxa-2,5,8-triazaoctadecanedioate, 1-tricyclo[3.3.1.1$^{3,7}$]dec-2-yl 16-ethyl-3-(1H-indol-3-yl-methyl)-3-methyl-4,9,12-trioxo-7-phenyl-13-oxa-2,5,8,16-tetraazaoctadecanoate, bis(tricyclo[3.3.1.1$^{3,7}$]dec-2-yl) 3,25-bis(1H-indol- 3-yl-methyl)-3,25-dimethyl-4,9,12,16,19,24 -hexaoxo-7,21-diphenyl-13,15-dioxa-2,5,8,20,23,26 -hexaazaheptacosanedioate, tricyclo[3.3.1.1$^{3,7}$]dec-2-yl 3-(1H-indol-3 -ylmethyl)-3-methyl-4,9,12,16-tetraoxo-7-phenyl-13,15 -dioxa-2,5,8-triazaheptadecanoate, tricyclo[3.3.1.1$^{3,7}$]dec-2-yl 3-(1H-indol-3 -ylmethyl)-3-methyl-4,9,12,16,-tetraoxo-7-phenyl-13,15 -dioxa-2,5,8-triazaoctadecanoate, tricyclo[3.3.1.1$^{3,7}$]dec-2-yl 3-(1H-indol-3 -ylmethyl)-3-methyl-4,9,12,16-tetraoxo-7-phenyl-13,15 -dioxa-2,5,8-triazanonadecanoate, 1-tricyclo[3.3.1.1$^{3,7}$]dec-2-yl 3-(1H-indol-3 -ylmethyl)-3-methyl-4,6,11-trioxo-9-phenyl-13,15-dioxa-2,5,7,10-tetraazatetraadecandioate, 14-anhydride with 2-methylpropanoic acid, tricyclo[3.3.1.1$^{3,7}$]dec-2-yl 3-(1H-indol-3 -ylmethyl)-3-methyl-4,9,12,16-tetraoxo-7-phenyl-13,15 -dioxa-2,5,8-triazaeicosanoate, tricyclo[3.3.1.1$^{3,7}$]dec-2-yl 3-(1H-indol-3 -ylmethyl)-3-methyl-4,9,12,16-tetraoxo-7,16-diphenyl-13,15dioxa-2,5,8-triazahexadecanoate, 2,3-dihydro-1H-inden-5-yl 4-[[2-[[3-(1H-indol-3 -yl)-2-methyl-1-oxo-2-[[(tricyclo[3.3.1.1$^{3,7}$]dec-2 -yloxy)carbonyl]amino]propyl]amino]-1-phenylethyl]-amino]-4-oxobutanoate, tricyclo[3.3.1.1$^{3,7}$]dec-2-yl 14-(2,2-dimethyl-1,3 -dioxolan-4-yl)-3-(1H-indol-3-ylmethyl)-3-methyl-4,9,12-trioxo-7-phenyl-13-oxa-2,5,8 -triazatetradecanoate, 1-ethyl 16-tricyclo[3.3.1.1$^{3,7}$]dec-2-yl 14-(1H-indol-3-yl-methyl)-3,14-dimethyl-5,8,13-trioxa-10-phenyl-2,4-dioxa-9,12,15-triaazahexadecanedioate, 1,3-dihydro-3-oxo-1-isobenzofuranyl 4-[[2-[[3 -(1H-indol-3-yl)-2-methyl-1-oxo-2-[[(tricyclo-[3.3.1.1$^{3,7}$]dec-2-yloxy)carbonyl]amino]propyl]amino]-1 -phenylethyl]amino]-4-oxobutanoate, tricyclo[3.3.1.1$^{3,7}$]dec-2-yl 17-amino-3-(1H-indol-3-ylmethyl)-3,18-dimethyl-4,9,12,16-tetraoxo-7-phenyl-13,15-dioxa-2,5,8-triazanonadecanedioate, 19-methyl 1-tricyclo[3.3.1.1$^{3,7}$]dec-2-yl 17-amino-3-(1H-indol-3-ylmethyl)-3-methyl-4,9,12,16-tetraoxo-7 -phenyl-13,15-dioxa-2,5,8-triazanonadecanedioate, N$^5$-[2-[2-[[3-(1H-indol-3-yl)-2-methyl-1-oxo-2-[[(tricyclo[3.3.1.1$^{3,7}$]dec-2-yloxy)carbonyl]amino]-propyl]amino]ethyl]phenyl]-L-glutamine, N$^5$-[[2-[2-[[3-(1H-indol-3-yl)-2-methyl-1-oxo-2 -[[(tricyclo[3.3.1.1$^{3,7}$]dec-2-yloxy)carbonyl]amino]-propyl]amino]ethyl]phenyl]methyl]-L-glutamine, tricyclo[3.3.1.1$^{3,7}$]dec-2-yl [1-(1H-indol-3 -ylmethyl)-1-methyl-2-oxo-2-[[2-[2-[()propylamino)-acetyl]amino]phenyl]ethyl]amino]ethyl]carbamate, tricyclo[3.3.1.1$^{3,7}$]dec-2-yl [1-(1H-indol-3 -ylmethyl)-1-methyl-2-oxo-2-[[2-[2-[[(propylamino)-acetyl]amino]methyl]phenyl]ethyl]amino]ethyl]-carbamate, tricyclo[3.3.1.1$^{3,7}$]dec-2-yl [1-indol-3 -ylmethyl)-1-methyl-2-[[2-[2-[(1-methyl-3-oxo-1 -butenyl)amino]phenyl]ethyl]amino]-2-oxoethyl]-carbamate, tricyclo[3.3.1.1$^{3,7}$]dec-2-yl [1-(1H-indol-3 -ylmethyl)-1-methyl-2-[[2-[2-[[(1-methyl-3-oxo-1 -butenyl)amino]methyl]phenyl]ethyl]amino]-2 -oxoethyl]carbamate, ethyl 3-[[2-[2-[[3-(1H-indol-3-yl)-2-methyl-1 -oxo-2-[[(tricyclo[3.3.1.1$^{3,7}$]dec-2-yloxy)carbonyl]-amino]propyl]amino]ethyl]phenyl]amino]-2-butenoate, ethyl 3-[[[2-[2-[[3-(1H-indol-3-yl)-2-methyl-1 -oxo-2-[[(tricyclo[3.3.1.1$^{3,7}$]dec-2-yloxy)carbonyl]-amino]propyl]amino]ethyl]phenyl]methyl]amino]-2 -butenoate, 1,1-dimethylethyl 3-[[2-[2-[[3-(1H-indol-3-yl)-2 -methyl-1-oxo-2-[[(tricyclo[3.3.1.1$^{3,7}$]dec-2-yloxy)-carbonyl]amino]propyl]amino]ethyl]phenyl]amino]-2 -butenoate, and 1,1-dimethylethyl 3-[[[2-[2-[[3-(1H-indol-3-yl)-2 -methyl-1-oxo-2-[[(tricyclo[3.3.1.1$^{3,7}$]dec-2 -yloxy)carbonyl]amino]propyl]amino]ethyl]phenyl-methyl]amino]-2-butenoate.

Most especially preferred compounds of the instant invention are:

L-glutamic acid, N-[N-[α-methyl-N-[(tricyclo-[3.3.1.1$^{3,7}$]dec-2-yloxy)carbonyl]-D-tryptophyl]-L-phenylalanyl]-, 2-[[3-(1H-indol-3-yl)-2-methyl-1-oxo-2[[tricyclo-[3.3.1.1$^{3,7}$]dec-2-yloxy)carbonyl]amino]propyl]amino]-3 -phenylpropyl(R-(R*,S*)]-1,4-dihydro-1-methyl-3 -pyridinecarboxylate, 2-[[(3-(1H-indol-3-yl)-2-methyl-1-oxo-2[()tricyclo [3.3.1.1$^{3,7}$]dec-2-yloxy)carbonyl]amino]-propyl]amino]-3-phenylpropyl[R-(R*,S*)]-trigonelline iodide, and 2-[3-[3-(1H-indol-3-yl)-2-methyl-1-oxo-2 -[[tricyclo [3.3.1.1$^{3,7}$]dec-2-yloxy)carbonyl]amino]-propyl]amino]-3-phenylpropyl[R-(R*,S*)]-3 -pyridinecarboxylate.

Also preferred compounds are:

1,2-dihydro-2-methyl-4-isoquinolinecarboxylic acid, 3-(1H-indol-3-ylmethyl)-3-methyl-1,4,9,12 -tetraoxo-7-phenyl-1-(tricyclo[3.3.1.1$^{3,7}$]dec-2-yloxy)-13-oxa-2,5,8-triazapentadec-15-yl ester, 4-[[2-[[3-(1H-indol-3-yl)-2-methyl-1-oxo-2 -[[(tricyclo [3.3.1.1$^{3,7}$]dec-2-yloxy)carbonyl]amino]-propyl]amino]-1-phenylethyl]amino]-4-oxobutanoic acid, 2-[[(1,4-dihydro-1-methyl-3-pyridinyl)carbonyl]amino]-ethyl ester, 4-[[2-[[3-(1H-indol-3-yl)-2-methyl-1-oxo-2 -[[(tricyclo [3.3.1.1$^{3,7}$]dec-2-yloxy)carbonyl]amino]-propyl]amino]-1-phenylethyl]amino]-4-oxobutanoic acid, 2-[[(1,2-dihydro-2-methyl-4-isoquinolinyl)carbonyl]-amino]ethyl ester, 1,2-dihydro-2-methyl-4-isoquinolinecarboxylic acid, 3-(1H-indol-3-ylmethyl)-3-methyl-1,4,9,12 -tetraoxo-7-phenyl-1(tricyclo[3.3.1.1$^{3,7}$]dec-2-yloxy)-13-oxa-2,5,8-triazapentadec-10-en-15-yl ester, 4-[[2-[[3-(1H-indol-3-yl)-2-methyl-1-oxo-2 -[[(tricyclo [3.3.1.1$^{3,7}$]dec-2-yloxy)carbonyl]amino]-propyl]amino]-1-phenylethyl]amino]-4-oxo-2-butenoic acid, 2-[[(1,4-dihydro-1-methyl-3-pyridinyl)carbonyl]-amino]ethyl ester, 11,4-dihydro-1-methyl-3-pyridinecarboxylic acid, 2-[3-[[3-(1H-indol-3-yl)-2-methyl-1-oxo-2-[[(tricyclo-[3.3.1.1$^{3,7}$] dec-2-yloxy)carbonyl]amino]propyl]amino]-1 -oxo-4-phenylbutoxy]ethyl ester, 1,4-dihydro-1-methyl-3-pyridinecarboxylic acid, 2-[[3-(1H-indol-3-yl)-2-methyl-1-oxo-2-[[(tricyclo-[3.3.1.1$^{3,7}$] dec-2-yloxy)carbonyl]amino]propyl]amino]-3 -phenylpropyl ester, 1,4-dihydro-1-methyl-3-pyridinecarboxylic acid, 3-(1H-indol-3-ylmethyl)-3-methyl-1,4,9,12-tetraoxo-7 -phenyl-1-(tricyclo[3.3.1.1$^{3,7}$]dec-2-yloxy)-13-oxa-2,5,8-triazapentadec-15-yl ester, 1,4-dihydro-1-methyl-3-pyridinecarboxylic acid, 3-(1H-indol-3-ylmethyl)-3-methyl-1,4,9,12-tetraoxo-7 -phenyl-1-(tricyclo[3.3.1.1$^{3,7}$]dec-2-yloxy)-13-oxa-2,5,8-triazatetradec-14-yl ester, 1,4-dihydro-1-methyl-3-pyridinecarboxylic acid, 3-(1H-indol-3-ylmethyl)-3-methyl-1,4,9,12-tetraoxo-7 -phenyl-1-(tricyclo[3.3.1.1$^{3,7}$]dec-2-yloxy)-13-oxa-2,5,8-triazapentadec-10-en-15-yl ester, 1,4-dihydro-1-methyl-3-pyridinecarboxylic acid, 3-(1H-indol-3-ylmethyl)-3-methyl-1,4,9,12-tetraoxo-7 -phenyl-1-(tricyclo[3.3.1.1$^{3,7}$]dec-2-yloxy)-13-oxa-2,5,8-triazatetradex-10-en-14-yl ester, butanoic acid, 4-[[2-[[3-(1H-indol-3-yl)-2 -methyl-1-oxo-2-[[)tricyclo[3.3.1.1$^{3,7}$]dec-2-yloxy)carbonyl]amino]propyl]amino]-1 -phenylethyl]amino]-4-oxo-, (2,2-dimethyl-1 -oxopropoxy)methyl ester, [R-(R*,R*)]-, butanoic acid, 4-[[2-[[3-(1H-indol-3-yl)-2 -methyl-1-oxo-2-[[(tricyclo[3.3.1.1$^{3,7}$]dec-2-yloxy)carbonyl]amino]propyl]amino]ethyl]amino]-4-oxo-, chloromethyl ester, [R-(R*, R*)]-, pentanedioic acid, [4-[[2-[[3-(1H-indol-3-yl)-2 -methyl-1-oxo-2-[[(tricyclo[3.3.1.1$^{3,7}$]dec-2-yloxy)-carbonyl] amino]propyl]amino]-1-phenylethyl]amino]-1,4 -dioxobutoxy]methyl ester, [R-(R*,R*)-, compd. with 1-deoxy-1-(methylamino)-D-glucitol, butanoic acid, 4-[[2-[[3-(1H-indol-3-yl)-2 -methyl-1-oxo-2-[[(tricyclo[3.3.1.1$^{3,7}$]dec-2 -yloxy)carbonyl]amino]propyl]amino]-1 -phenylethyl]amino]-4-oxo-2,3-dihydro-1H-inden-5-yl ester, [R-(R*,R*)]-, and butanoic acid, 4-[[2-[[3-(1H-indol-3-yl)-2 -methyl-1-oxo-2-[[(tricyclo[3.3.1.1$^{3,7}$]dec-2-yloxy)carbonyl]amino]propyl]amino]-1 -phenylethyl]amino]-4-oxo-, 2-(diethylamino)ethyl ester, [R-(R*,R*)]-.

The compounds of the present invention include compounds of formula I wherein the indole moiety is a 2- or 3-indolyl.

The compounds include solvates and hydrates and pharmaceutically acceptable salts of the compounds of formula I.

The compounds of the present invention can have multiple chiral centers including those designated in the above formula I by a ‡, ‡, † depending on their structures. For example, when $R^3$ taken with $R^{12}$ and $R^4$ taken with $R^{13}$ form double bonds to these carbon atoms they are no longer chiral. In addition, centers of asymmetry may exist on substituents $R^1, R^9$, $R^3$, $R^4$ and/or Ar. In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by convention method well known in the art such as conversion to a salt with an optically active compound, followed by separation by chromatography or recrystallization and reconversion to the nonsalt form.

Biologically significant amino acids are illustrated in Table I below.

TABLE I

| Biologically Significant Amino Acids* | |
|---|---|
| Alanine | Isoleucine |
| β-Alanine | Isovaline |
| Alloisoleucine | Leucine |
| Allthreonine | Lysine |
| Arginine | Methionine |
| Asparagine | Norleucine |
| Aspartic Acid | Norvaline |
| Cysteine | Ornithine |
| Glutamic Acid | Phenylalanine |
| Glutamine | Proline |
| Glycine | Serine |
| Histidine | Threonine |
| Romocysteine | Tyrosine |
| Homosexine | Tryptophan |
| | Valine |

*The side of alanine is $CH_3$— and of aspartic acid is HOOC—$CH_2$— and so forth.

Pharmaceutically acceptable counter cations or anions are shown below:

Acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoata (embonate), pantothenate, phosphate/diphosphate, polygalacturonate, salicylate, stearate, subacetate, succinate, sulfate, tannata, tartrate, teoclate, triethiodide, benzathine, chloroprocaine, choline, diethanolamine, ethylenediamine, meglumine, procaine, aluminum, calcium lithium magnesium, potassium, sodium, and zinc.

The compounds of the present invention can be formed by coupling individual substituted ∝-amino acids by methods well known in the art. (See, for example, standard synthetic methods discussed in the multi-volume treatise "The Peptides, Analysis, Synthesis, Biology," by Gross and Meienhofer, Academic Press, New York.) The individual substituted alpha amino acid starting materials are generally known or, if not know, may be synthesized and, if desired, resolved by methods within the skill of the art. (Synthesis of racemic [DL]-∝-methyl tryptophan methyl ester—see Braña, M. F., et al, *J. Heterocyclic Chem.* 17:829, 1980.)

A key intermediate in the preparation of compounds of formula I is a compound of formula

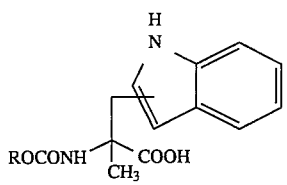

II wherein R is selected from $R^1$, 9-fluorenylmethyl, Bz and other suitable N-blocking groups. These are useful as intermediates in the preparation of compounds of formula I. The compounds wherein R is 1-adamantyl, 2-adamantyl, 4-protoadamantyl, exo-bornyl, endo-bornyl, exo-norbornyl, endo-norbornyl, 2-methylcyclohexyl, 2-chlorocyclohexyl, or camphoryl are novel and are preferred.

The disclosure of U.S. Pat. No. 4,757,151 is hereby incorporated by reference. It describes the 9-fluorenylmethyl blocking group.

Compounds of formula II are prepared by reacting

ROH      III wherein R is as defined above, with phosgene or a phosgene substitute to produce a corresponding compound of formula ROCOCl      IV and then reacting a compound of formula IV with ∝-methyltryptophan to produce the desired compound of formula II above.

Alternatively, a compound of formula IV can be reacted with an ∝-methyltryptophan methyl ester to produce

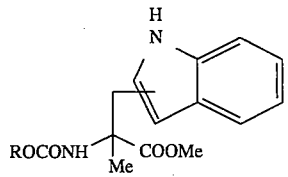

V which can be converted to a compound of formula II by known means such as hydrolysis with aqueous lithium hydroxide.

Novel intermediates of the instant invention include compounds of formula

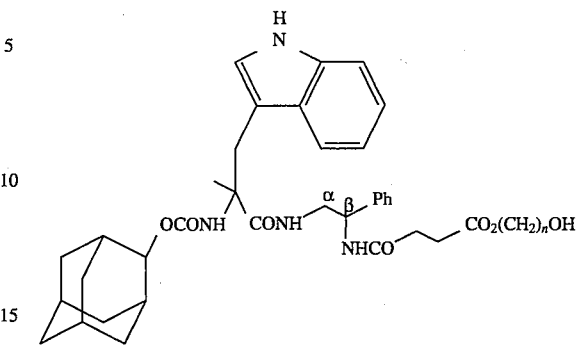

VI wherein n=1–3 and

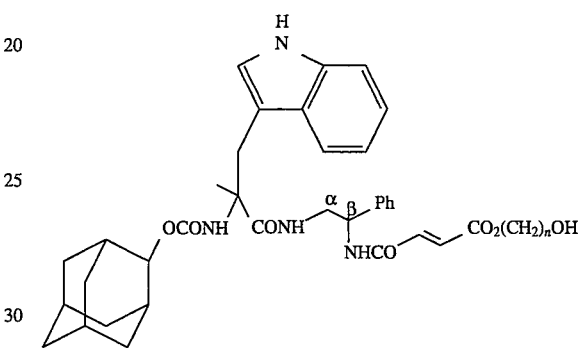

VII

This includes also α positions in both formulae. Further, the moiety of formula VIII

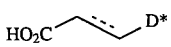

provides novel intermediates.

The compounds in Schemes I and Ia below were prepared by solution synthesis, from the C-terminus, using standard peptide protocols, and illustrated by the synthesis of 2-adamantyloxycarbonyl-D-a-methyltryptophenyl-L-alanyl-β-alanine (6a) (see Scheme I).

SCHEME I

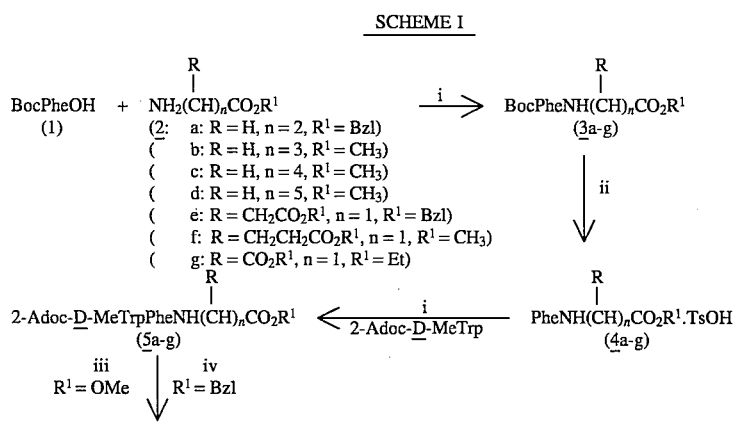

-continued
SCHEME I

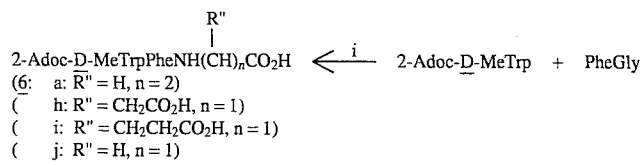

2-Adoc-D-MeTrpPheNH(CH)ₙCO₂H  ⟵ⁱ—  2-Adoc-D-MeTrp  +  PheGly
(6: a: R" = H, n = 2)
( h: R" = CH₂CO₂H, n = 1)
( i: R" = CH₂CH₂CO₂H, n = 1)
( j: R" = H, n = 1)

Reagents and conditions:
i) WSCDJ(DCCI), HOSt·H₂O, DIPEA, CH₂Cl₂(EtOAc)
ii) TsOH·H₂O, CH₂Cl₂-THF or TFA, CH₂Cl₂
iii) 0.1N OH⁻, THF
iv 10% Pd-C, MeOH, 1,4 cyclohexadiene Scheme Ia below describes synthetic steps towards compounds of type 10 and 11, a, d, l, Example 5–10 inclusive. S-2-tert-Butyloxycarbonylamino-3-phenylpropionic acid 7 was condensed with, for example, glycine ethyl ester 2k to give the amide 8k. Removal of the tBoc protecting group with tridluoroacetic acid gave the free amine 9k which was condensed with 2-adamantyloxycarbonyl-R-α-methyltryptophan to give 10k (Example 6) which was saponified using lithium hydroxide to the carboxylic acid 11k (Example 9).

SCHEME IA

Boc-L-NHCH(CH₂Ph)CH₂CO₂H   +   NH₂(CH₂)ₙCO₂R
(7)                              (2:  a: n = 2, R = CH₃
                                  (  k: n = 1, R = C₂H₅)
                                  (  l: n = 3, R = C₂H₅)

↓ i

-continued
SCHEME IA

Boc-L-NHCH(CH₂Ph)CH₂CONH(CH₂)ₙCO₂R
(8 a,k,l)

↓ ii

L-NHCH(CH₂Ph)CH₂CONH(CH₂)ₙCO₂R
(9 a,k,l)

↓ i

2-Adoc-D-MeTrp-L-NHCH(CH₂Ph)CH₂CONH(CH₂)ₙCO₂R
(10 a,k,l)

↓ i

2-Adoc-D-MeTrp-L-NHCH(CH₂Ph)CH₂CONH(CH₂)ₙCO₂H
(11 a,k,l)

↓

SCHEME II
(See Example 16)

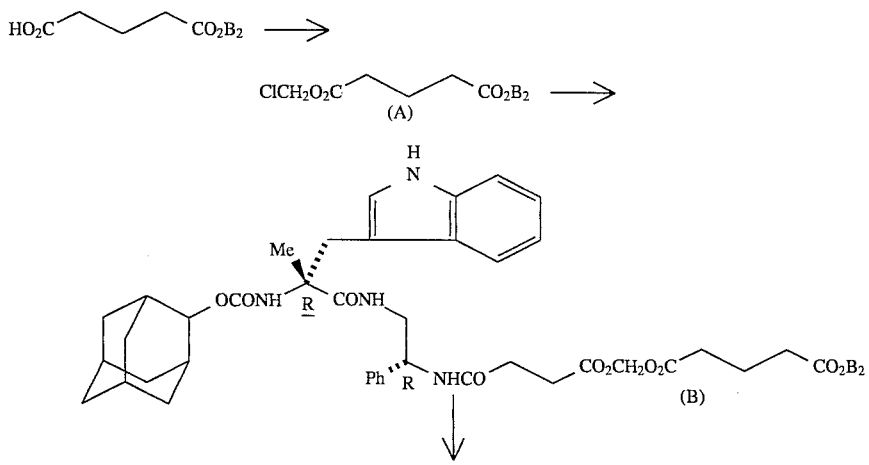

-continued
SCHEME II
(See Example 16)

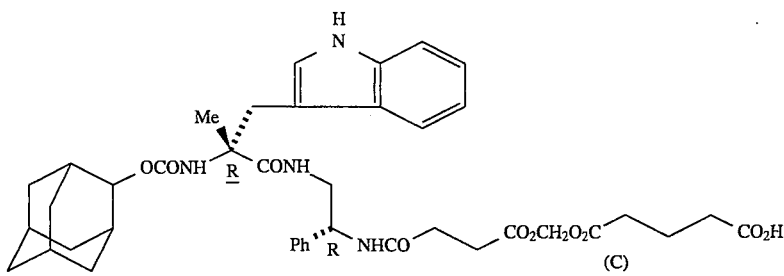

(C)

Scheme III below illustrates procedures for preparing final products of the instant invention. The following compounds can be prepared using Method A:

tricyclo[3.3.1.1³,⁷]dec-2-yl 3-(1H-indol-3 -ylmethyl)-3, 17,17-trimethyl-4,9,12,16-tetraoxo-7 -phenyl-13,15-dioxa-2,5,8-triazaoctadecanoate, 1-tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazaeicosanedioate, 1-tricyclo[3.3.1.1³,⁷]dec-2-yl 3-(1H-indol-3 -ylmethyl)-3, 17,17-trimethyl-4,9,12,16-tetraoxo-7 -phenyl-13,15-dioxa-2,5,8-triazaoctadecanedioate, bis(tricyclo[3.3.1.1³,⁷]dec-2-yl) 3,25-bis(1H-indol- 3-ylmethyl)-3,25-dimethyl-4,9,12,16,19,24 -hexaoxo-7,21-diphenyl13,15-dioxa-2,5,8,20,23,26 -hexaazaheptacosanedioate, tricyclo[3.3.1.1³,⁷]dec-2-yl 3-(1H-indol-3 -ylmethyl)-3-methyl-4,9,12,16-tetraoxo-7-phenyl-113,15 -dioxa-2,5,8-triazaheptadecanoate, tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazaoctadecanoate, tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazanonadecanoate, 1-tricyclo[3.3.1.1³,⁷]dec-2-yl 3-(1H-indol-3 -ylmethyl)-3-methyl-4,6,11-trioxo-9-phenyl-13,15-dioxa-2,5,7,10-tetraazatetraadecandioate, 14-anhydride with 2-methylpropanoic acid, tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazaeicosanoate, tricyclo[3.3.1.1³,⁷]dec-2-yl 3-(1H-indol-3 -ylmethyl)-3-methyl-4,9,12,16-tetraoxo-7,16-diphenyl-13,15-dioxa-2,5, 8-triazahexadecanoate, tricyclo[3.3.1.1³,⁷]dec-2-yl 17-amino-3-(1H-indol-3-ylmethyl)-3,18-dimethyl-4,9,12,16-tetraoxo-7-phenyl-13,15-dioxa-2,5,8-triazanonadecanedioate, and 19-methyl 1-tricyclo[3.3.1.1³,⁷]dec-2-yl 17-amino-3-(1H-indol-3-ylmethyl)-3-methyl-4,9,12,16-tetraoxo-7 -phenyl-13,15-dioxa-2,5,8-triazanonadecanedioate.

The following compounds can be prepared using Method B:

tricyclo[3.3.1.1³,⁷]dec-2-yl 3-(1H-indol-3 -ylmethyl)-3, 17,17-trimethyl-4,9,12,16-tetraoxo-7 -phenyl-13,15-dioxa-2,5,8-triazaoctadecanoate, tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazaheptadecanoate, tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazaoctadecanoate, tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazanonadecanoate, 1-tricyclo[3.3.1.1³,⁷]dec-2-yl 3-(1H-indol-3 -ylmethyl)-3-methyl-4,6,11-trioxo-9-phenyl-13,15-dioxa-2,5,7,10-tetraazatetraadecandioate, 14-anhydride with 2-methylpropanoic acid, tricyclo[3.3.1.1³,⁷]dec-2-yl 3-(1H-indol-3 -ylmethyl)-3-methyl-4,9,12,16-tetraoxo-7-phenyl-13,15 -dioxa-2,5,8-triazaeicosanoate, tricyclo[3.3.1.1³,⁷]dec-2-yl 3-(1H-indol-3 -ylmethyl)-3-methyl-4,9,12,16-tetraoxo-7,16-diphenyl-13,15-dioxa-2,5, 8-triazahexadecanoate, 1-ethyl 16-tricyclo[3.3.1.1³,⁷]dec-2-yl 14-(1H)-indol-3-ylmethyl)-3,14-dimethyl-5,8,13-trioxa-10 -phenyl-2,4-dioxa-9,12,15-triaazahexadecanedioate, tricyclo[3.3.1.1³,⁷]dec-2-yl 17-amino-3-(1H-indol-3-ylmethyl)-3,18-dimethyl-4,9,12,16-tetraoxo-7-phenyl-13,15-dioxa-2,5,8-triazanonadecanedioate, and 19-methyl 1-tricyclo[3.3.1.1³,⁷]dec-2-yl 17-amino-3-(1H-indol-3-ylmethyl)-3-methyl-4,9,12,16-tetraoxo-7 -phenyl-13,15-dioxa-2,5,8-triazanonadecanedioate.

The following compounds can be prepared using Method C:

1-tricyclo[3.3.1.1³,⁷]dec-2-yl 16-ethyl-3-(1H-indol- 3-ylmethyl)-3-methyl-4,9,12-trioxo-7-phenyl-13 -oxa-2,5,8,16-tetraazaoctadecanoate, 2,3-dihydro-1H-inden-5-yl 4-[[2-[[3-(1H-indol-3 -yl)-2-methyl-1-oxo-2-[[(tricyclo[3.3.1.1³,⁷]dec-2-yloxy)carbonyl]amino]propyl]amino]-1-phenylethyl]-amino]-4-oxobutanoate, tricyclo[3.3.1.1³,⁷]dec-2-yl 14-(2,2-dimethyl-1,3 -dioxolan-4yl)-3-(1H-indol-3-ylmethyl)-3-methyl-4,9,12-trioxo-7phenyl-13-oxa-2,5,8 -triazatetradecanoate, and 1,3-dihydro-3-oxo-1-isobenzofuranyl 4-[[2-[[3 -(1H-indol-3-yl)-22-methyl-1-oxo-2-[[(tricyclo-[3.3.1.1³,⁷]dec-2-yloxy)carbonyl]amino]propyl]amino]-1 -phenylethyl] amino]-4-oxobutanoate.

The following compounds can be prepared using Method D:

$N^5$-[2-[2-[[3-(1H-indol-3-yl)-2-methyl-1-oxo-2 -[[(tricyclo[3.3.1.1³,⁷]dec-2-yloxy)carbonyl]amino]-propyl] amino]ethyl]phenyl]-L-glutamine, $N^5$-[[2-[2-[[3-(1H-indol-3-yl)-2-methyl-1-oxo-2 -[[(tricyclo[3.3.1.1³,⁷]dec-2-yloxy)carbonyl]amino]-propyl] amino]ethyl]phenyl]methyl]-L-glutamine, tricyclo[3.3.1.1³,⁷]dec-2-yl [1-(1H-indol-3 -ylmethyl)-1-methyl-2-oxo-2-[[2-2-[[(propylamino)-acetyl]amino]phenyl]ethyl]amino]ethyl]carbamate, and tricyclo[3.3.1.1³,⁷]dec-2-yl [1-(1H-indol-3 -ylmethyl)-1-methyl-2-oxo-2-[[2-2-[[[(propylamino)-acetyl]amino]methyl]phenyl]ethyl]amino]ethyl]-carbamate.

The following compounds can be prepared using Method E:

tricyclo[3.3.1.1$^{3,7}$]dec-2-yl [1-(1H-indol-3-ylmethyl)-1-methyl-2-[[2-[2-[)1-methyl-3-oxo-1-butenyl)amino]phenyl]ethyl]amino]-2-oxoethyl]-carbamate, tricyclo[3.3.1.1$^{3,7}$]dec-2-yl [1-(1H-indol-3-ylmethyl)-1-methyl-2-[[2-[2-[[)1-methyl-3-oxo-1-butenyl)amino]methyl]phenyl]ethyl]amino]-2-oxoethyl]carbamate, ethyl 3-[[2-[2-[[3-(1H-indol-3-yl)-2-methyl-1-oxo-2-[[(tricyclo[3.3.1.1$^{3,7}$]dec-2-yloxy)carbonyl]-amino]propyl]amino]ethyl]phenyl]amino]-2-butenoate, ethyl 3-[[[2-[2-[[3-(1H-indol-3-yl)-2-methyl-1-oxo-2-[[(tricyclo[3.3.1.1$^{3,7}$]dec-2-yloxy)carbonyl]-amino]propyl]amino]ethyl]phenyl]methyl]amino]-2-butenoate, 1,1-dimethylethyl 3-[[2-[2-[[3-(1H-indol-3-yl)-2-methyl-1-oxo-2-[[(tricyclo[3.3.1.1$^{3,7}$]dec-2-yloxy)-carbonyl]amino]propyl]amino]ethyl]phenyl]amino]-2-butenoate, and 1,1-dimethylethyl 3-[[[2-[2-[[3-(1H-indol-3-yl)-2-methyl-1-oxo-2-[[(tricyclo[3.3.1.1$^{3,7}$]dec-2-yloxy)carbonyl]amino]propyl]amino]ethyl]phenyl]-methyl]amino]-2-butenoate.

CCK receptors have been shown to exist in the central nervous system. (See Hays et al, *Neuropeptides* 1:53–62, 1980; and Satuer et al, *Science* 208:1155–1156, 1980).

In this screening test, the cerebral cortices taken from male CFLP mice weighing between 30–40 g were dissected on ice, weighed, and homogenized in 10 volumes of 50 mM Tris-HCl buffer (pH 7.4 at 0°–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM MgCl$_2$, 1 nM EDTA, 5 mg/mL bovine albumin, and bacitracin (0.25 mg/mL).

In saturation studies, cerebral cortical membranes were incubated at 23° C. for 120 minutes in a final volume of 500 μL of Hepes incubation buffer (pH 7.2) together with 0.2–20 nM tritiated-pentagastrin (Amersham International, England).

In the displacement experiments, membranes were incubated with a single concentration (2 nM) of ligand, together

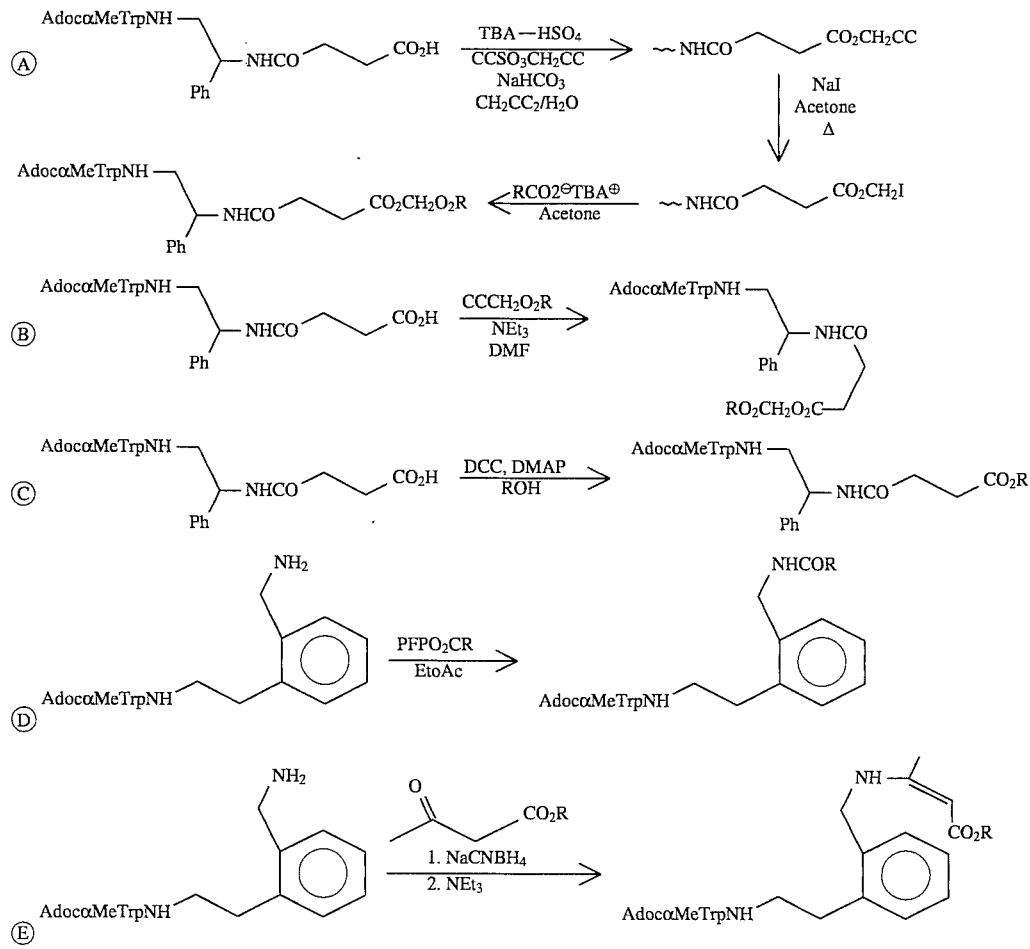

BIOLOGICAL ACTIVITY

The biological activity of compounds of the present invention was evaluated employing an initial screening test which rapidly and accurately measured the binding of the tested compound to known CCK receptor sites. Specific with increasing concentrations ($10^{-11}$ to $10^{-14}$M) of competitive test compound. In each case, the nonspecific binding was defined as that persisting in the presence of the unlabeled octapeptide CCK$_{26-33}$ ($10^{-6}$M).

Following incubation, radioactivity bound to membranes were separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47–52%).

The specific binding to CCK receptor sites was defined as the total bound tritiated-pentagastrin minus the amount of tritiated-pentagastrin bound in the presence of $10^{-6}$ octapeptide, $CCK_{26-33}$.

Saturation curves for specific tritiated-pentagastrin binding to mouse cortical membranes were analyzed by the methods of Scatchard (*Ann. New York Acad. Sci.* 51:660–672, 1949, and Hill (*J. Physiol.* 40:IV–VIII, 1910, to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson and Redbard, 1978) to provide estimates of the $IC_{50}$ and nH (apparent Hill coefficient) values). ($IC_{50}$ values were defined as the concentration of test compound required to produce 50% inhibition of specific binding.)

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds are presented in Table II below.

TABLE II

| Compound* Number | Receptor Affinity CCI—B/nM | n |
| --- | --- | --- |
| 6a | 27.9 ± 4.1 | 3 |
| 6h | 1170 | 2 |
| 6i | 1520 | 1 |
| 6j | 7.41 ± 1.04 | 3 |
| 5f | 110 | 2 |
| 5d | 173 | 2 |
| 10a | 21.2 ± 5.4 | 3 |
| 10k | 17.9 | 1 |
| 10l | 66.4 | 2 |
| 11a | 9.44 | 2 |
| 11k | 4.4 ± 0.6 | 3 |
| 11l | 10.6 ± 0.12 | 3 |

*Compound as numbered in Schemes I and IA.
n = Number of assays

Compounds of the present invention are useful as appetite suppressants as based on the tests described hereinbelow.

In the Palatable Diet Feeding assay, adult male Hooded Lister rats weighing between 200–400 g are housed individually and trained to eat a palatable diet. This diet consists of Nestlés sweetened condensed milk, powdered rat food and rat water which when blended together set to a firm consistency. Each rat is presented with 20–30 g of the palatable diet for 30 minutes per day during the light phase of the light–dark cycle over a training period of five days. The intake of palatable diet is measured by weighing the food container before and after the 30-minute access period (limits of accuracy 0.1 g). Care is taken to collect and correct for any spillage of the diet. Rats have free access to pellet food and water except during the 30-minute test period.

After the training period, dose-response curves are constructed for CCK8 and several representative compounds of the present invention (n=8–10 rats per dose level). $MPE_{50}$ values (±95% confidence limits) are obtained for the anorectic effects of these compounds. In therapeutic use as appetite suppression agents, the compounds of the instant invention are administered to the patient at dosage levels of from about 200 to about 2800 mg per day.

Male Hooded Lister rats (175–250 g) are housed individually and fasted overnight (free access to water). They are anesthetized with urethane (1.5 g/kg IP) and the trachea cannulated to aid spontaneous respiration. The stomach is perfused continuously using a modification of the original method of Ghosh & Schild in "Continuous recording of acid secretion in the rat", *Brit. J. Pharmac.* 13:54–61, 1956 as described by Parsons in "Quantitative studies of drug-induced gastric acid secretion". (Ph.D. Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37°±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 mL/kg washed in with 0.15 mL 0.9% w/v NaCl. Basal pH is allowed to stabilize before administration of compounds is begun. Typically 30 minutes elapses between surgery and the first compound administration.

The compounds of the instant invention are also useful as antiulcer agents as discussed hereinbelow.

Aspirin-induced gastric damage is assessed in groups of 10 rats each.

All animals are fasted for 24 hours before and throughout the experiment. Drug or vehicle is given 10 minutes before an oral dose of 1 mL of a 45-mg/mL suspension of aspirin in 0.5% carboxymethylcellulose (CMC).

The animals are sacrificed 5 hours after aspirin administration and the stomachs removed and opened for examination.

Gastric damage is scored as follows:

| Score | |
| --- | --- |
| 1 | Small hemorrhage |
| 2 | Large hemorrhage |
| 3 | Small ulcer |
| 4 | Large ulcer |
| 5 | Perforated ulcer |

The specific dosages employed, however, may be varied depending upon the patient, the severity of the condition being treated, and the activity of the compound employed. Determination of optimum dosages is within the skill of the art.

The compounds of the instant invention are also useful as anxiolytic agents as described and discussed below.

Anxiolytic activity is assessed in the light/dark exploration test in the mouse (B. J. Jones, et al, *Brit. J. Pharmacol.* 93:985–993, 1988).

The apparatus is an open-topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60-watt red bulb. The laboratory is illuminated with red light.

All tests are performed between 13 hundred hours, 0 minutes and 18 hundred hours, 0 minutes. Each mouse is tested by placing it in the center of the white area and allowing it to explore the novel environment for 5 minutes. Its behavior is recorded on videotape and the behavioral analysis is performed subsequently from the recording. Five parameters are measured: the latency to entry into the dark compartment, the time spent in each area, the number of transitions between compartments, the number of lines crossed in each compartment, and the number of rears in each compartment.

In this test an increase in the time spent in the light area is a sensitive measure of, that is directly related to, the anxiolytic effects of several standard anxiolytic drugs. Drugs are dissolved in water or saline and administered either subcutaneously, intraperitoneally, or by mouth (PO) via a stomach needle.

The compounds of the instant invention are useful as antipsychotic agents. Compounds are tested for their ability to reduce the effects of intra-accumbens amphetamine in the rat as described hereinafter.

Male Sprague Dawley (CD) Bradford strain rats are used. The rats were housed in groups of five at a temperature of 21°±2° C. on a 12 hour light–dark cycle of lights-on between 07 hours 00 minutes and 20 hours 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides are kept patent during a 14-day recovery period using stainless steel stylets, 0.3 mm diameter, which extended 0.5 mm beyond the guide tips.

Rats are manually restrained and the stylets removed. Intracerebral injection cannulae, 0.3 mm diameter, are inserted and drugs delivered in a volume of 0.5 μL over 5 seconds (a further 55 seconds was allowed for deposition) from Hamilton syringes attached via polythene tubing to the injection units. Animals are used on a single occasion only.

Behavioral experiments are conducted between 07 hours 30 minutes and 21 hours 30 minutes in a quiet room maintained at 22°±2° C. Rats are taken from the holding room and allowed 1 hour to adapt to the new environment. Locomotor activity is assessed in individual screened Perspex cages (25×15×15 cm (high) (banked in groups of 30) each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time animals are also observed for the presence of any nonspecific change in locomotor activity, e.g., sedation, prostration, stereotyped movements, that could interfere with the recording of locomotor activity.

The abilities of compounds to inhibit the hyperactivity caused by the injection of amphetamine into the nucleus accumbens of the rat are measured.

An increase in locomotor activity follows the bilateral injection of amphetamine (20 μg) into the nucleus accumbens; peak hyperactivity (50 to 60 counts 5 minutes$^{-1}$) occurs 20 to 40 minutes after injection.

Intraperitoneal injection of the rats with a compound (20 mg/kg or 30 mg/kg) or (10 mg/kg) reduces the hyperactivity caused by the intra-accumbens injection of amphetamine. This test is known to be predictive of antipsychotic activity (Costall, Domeney & Naylor & Tyers, Brit. J. Pharmac. 92:881–894).

The compounds of the instant invention prevent and treat the withdrawal response produced when chronic treatment by a drug is stopped or when alcohol abuse is stopped. These compounds are therefore useful as therapeutic agents in the treatment of chronic drug or alcohol abuse as discussed and described below.

The effect of the compounds of the instant invention is illustrated, for example, in the mouse "light/dark box" test.

Five animals are given nicotine, 0.1 mg/kg i.p. b.d. for 14 days. After a 24-hour withdrawal period, a compound is given at 1.0 mg/kg i.p. b.d. The increased time spent in the light area is a sensitive measure of the effect of the compound as an agent to treat withdrawal effects from nicotine.

The effect of long-term treatment and withdrawal from nicotine using a compound of the invention. Five mice are given nicotine at 0.1 mg/kg i.p. b.d. for 14 days. After a withdrawal period of 24 hours, the compound is given at 10 mg/kg i.p. b.d. The effect of the compound can be seen in the increase of time spent in the light area.

The effect of long-term treatment and withdrawal from diazepam with intervention with a compound of the invention is demonstrated by the following. Five mice are given diazepam, at 10 mg/kg i.p. b.d. for 7 days. Withdrawal is for a 24-hour period; the compound is given at 1.0 mg/kg i.p. b.d. The increased time spent in the light section shows the effect of the compound.

The effect of a compound of the invention on the long-term treatment and withdrawal from diazepam is demonstrated by the following. Five mice were given diazepam at 10 mg/kg i.p. b.d. for 7 days. After a withdrawal period of 24 hours, the compound is given at 10 mg/kg i.p. b.d. The amount of time spent in the light section after the compound is administered demonstrates the effectiveness of the compound.

The effect of a compound of the invention on the long-term treatment and withdrawal from alcohol is demonstrated by the following. Five mice are given alcohol in drinking water 8% w/v for 14 days. After a withdrawal period of 24 hours, the compound is given at 1.0 mg/kg i.p. b.d. The amount of time spent in the light section after the compound is administered demonstrates the effectiveness of the compound.

The effect of a compound of the invention on long-term treatment and withdrawal from alcohol is demonstrated by the following. Five mice were given alcohol in drinking water, 8% w/v for 14 days. After a withdrawal period of 24 hours, the compound is given at 10 mg/kg i.p. b.d. The increased time spent in the light section shows the effect of the compound on the mice.

The effectiveness in the long-term treatment and withdrawal from cocaine of a compound of the invention. Five mice are given cocaine as 1.0 mg/kg i.p. b.d. for 14 days. The increased time in the light section illustrates the effectiveness of the compound in the treatment.

The effect of long-term treatment and withdrawal from cocaine with the intervention of a compound of the invention is demonstrated by the following. Five mice are given cocaine at 1.0 mg/kg i.p. b.d. for 14 days after a withdrawal period of 24 hours, the compound is given at 1.0 mg/kg i.p. b.d. The effect of intervention with the compound is shown by the increase in time spent in the light section.

The anxiolytic effects of a compound of the invention is shown in the Rat Social Interaction Test on a dose range of 0.001 to 1.0 mg/kg when paired rats are dosed s.c. The anxiolytic effect of the compound are indicated by the increase in time spent in social interaction compared with the control value C. (Costall, B., University of Bradford)

The anxiolytic effects of a compound of the invention is shown in the Rat Elevated X-Maze Test on a dose range of 0.01 to 1.0 mg/kg s.c. The anxiolytic effect is indicated by the time spent in the open arm end section compared with control C.

Compounds of the invention depress the flexor response in a stimulated spinalized decerebrated rat preparation similar to morphine. The effect of giving a compound with morphine greatly potentiates the effect which lasts for 3 hours.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

A preferred pharmaceutically acceptable salt is the N-methyl glucamine salt.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

EXAMPLES

Example 1

(2-Adoc-D-MeTrp-L-Phe-B-Alanine (6a))

β-Alanine, N-[N-[α-methyl-N-[(tricyclo[3.3.1.1$^{3,7}$]-dec-2-yloxy)carbonyl]-D-tryptophyl]-L-phenylalanyl]

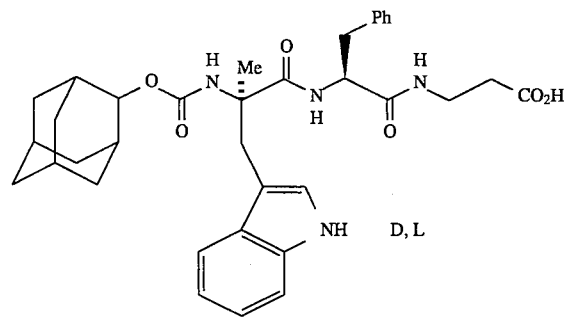

Boc-L-phenylalanyl-β-alanine, benzyl ester; (3a)

Boc-L-phenylalanine (1.32 g, 5.00 mmol) was dissolved in dichloromethane (50 mL) and treated with HoBt.H$_2$O (1.53 g, 2.00 mmol) followed by WSCDI (water soluble carbodiimide) (1.00 g, 5.24 mmol). After stirring for 40 minutes, β-alanine benzyl ester tosylate (1.85 g, 5.27 mmol) was added, followed by DIPEA (diisopropylethylamine) (1.29 g, 10 mmol). Stirring was continued overnight, then the solvent removed. The residue was dissolved in ethyl acetate (30 mL) and washed with water, 10% sodium bicarbonate solution, then 10% citric acid solution. The organic layer was dried (MgSO$_4$) and evaporated to a white solid—a single component by TLC, 1.74 g, 82% of (32). NMR (CDCl$_3$) δ 1.41 (9H, s), 2.47 (2H, m), 3.01 (2H, m), 3.45 (2H, m), 4.25 (1H, br.q), 5.00 (1H, br.s), 5.07 (2H, s), 6.21 (1H, br.t), 7.15–7.38 (10H, m).

L-Phenylalanyl-β-alanine benzyl ester tosylate (4a)

The solid described above was dissolved in CH$_2$Cl$_2$:THF (1:1, 50 mL) and treated with p-toluenesulphonic acid (1.62 g) at reflux for 2 hours following removal of the solvents. The residue was triturated with diethyl ether, giving a white powder, 1.87 g, 64%. NMR (D$_2$O) δ 2.38 (3H, s), 2.45 (2H, m), 3.03 (2H, m), 3.27 (1H, m), 3.49 (1H, m), 4.01 (1H, t), 5.12 (2H, s), 7.20–7.66 (12H, m), 7.97 (2H, d).

2-Adoc-D-MeTrp-L-Phe-β-Alanine benzyl ester (5a)

2-Adoc-D-MeTrp (1.00 g, 2.52 mmol) was dissolved in ethyl acetate (25 mL) and treated with HOBt.H$_2$O (400 mg, 2.61 mmol) and DCCI (550 mg, 2.66 mmol). After 30 minutes the mixture was filtered and the filtrate treated with (4a), produced above, followed by DIPEA (374 mg, 2.89 mmol). After stirring overnight, the mixture was filtered and the filtrate concentrated. The residue was chromatographed on silica (5% MeOH/CH$_2$Cl$_2$), giving 1.206 (68%) of product (5a). NMR (CDCl$_3$) δ 1.25 (3H, s), 1.53 (2H, br.d), 1.71–1.97 (12H, m), 2.54 (2H, m), 3.04 (2H, qd), 3.46 (2H, abq), 3.49 (2H, m), 4.67 (1H, q), 4.76 (1H, br.s), 4.94 (1H, s), 5.09 (2H, s), 6.21 (1H, d), 6.89 (1H, d), 6.99–7.36 (14H, m), 7.54 (1H, d), 8.20 (1H, s).

2-Adoc-D-Metrp-L-Phe-β-Alanine (6a)

500 mg of product (5a) was dissolved in methanol (20 mL) and the solution treated with 2,4-cyclohexadiene (2 mL) and 10% Pd/C (400 mg) and the mixture stirred until TLC revealed all starting material had been consumed. After filtering and concentration of the filtrate, the residue was purified by RP-HPLC (C$^{18}$, MeOH:H$_2$O-1:1), giving 267 mg of a white solid (6A), 63%. NMR (DMS-D$_6$) δ 1.05 (3H, s), 1.52 (2H, t), 1.71–2.04 (12H, m), 2.42 (2H, t), 2.74–3.31 (8H, m), 4.54 (1H, br.m), 4.75 (1H, s), 6.84–7.40 (12H, m), 7.84 (2H, m), 10.90 (1H, s); IR (CHBr$_3$ film) 1659, 1700 cm$^{-1}$.

The products (5 b–d, f, and g) were prepared in a similar manner to (5a).

2-Adoc-D-MeTrp-L-Phe-GABA-OMe (5b)

NMR (DMSO-d$_6$) δ 1.02 (3H, s), 1.48 (2H, 5), 1.62–2.07 (16H, m), 2.33 (2H, t), 2.90 (1H, t), 3.08 (3H, m), 3.30 (2H, m), 3.59 (3H, s), 4.52 (1H, m), 4.71 (1H, br.s), 6.87 (2H, m), 6.99 (1H, t), 7.16–7.35 (9H, m), 7.63 (1H, br.t), 7.83 (1H, br.d), 10.86 (1H, s).

2-Adoc-D-MeTrp-L-Phe-DAVA-OMe (5c)

NMR (DMSO-d$_6$) δ 1.03 (3H, s), 1.45–1.60 (6H, m), 1.69–1.98 (12H, m), 2.31 (2H, t), 2.91 (1H, t), 3.07 (3H, complex), 3.32 (3H, m), 3.58 (3H, s), 4.50 (1H, m), 4.71 (1H, br.s), 6.85–7.46 (1H, m), 7.76 (1H, br.d), 7.82 (1H, br.d), 10.85 1H, s).

2-Adoc-D-MeTrp-L-Phe-EACA-OMe (5d)

L-Phenylalaninamide, α-methyl-N-[(tricyclo[3.3.1.1$^{3,7}$]dec-2-yloxy)carbonyl]-D-tryptophyl-N-(6-methoxy-6-oxohexyl)-

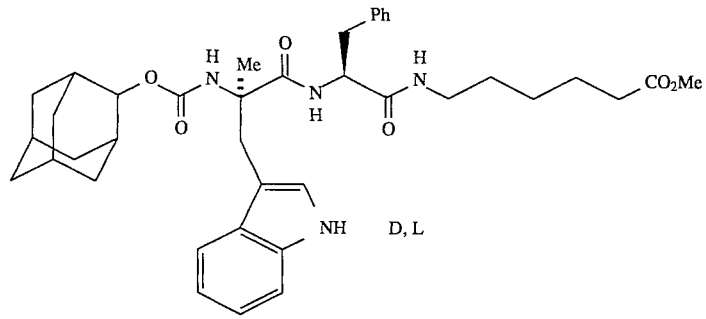

NMR (CDCl$_3$) δ 1.22 (3H, s), 1.29 (2H, m), 1.45–1.99 (16H, m), 3.0 (1H, dd), 3.21 (3H, m), 3.37 (2H, dd), 3.65 (3H, s), 4.72 (2H, m), 4.88 (1H, s), 6.19 (1H, d), 6.89–7.25 (11H, m), 7.36 (1H, d), 7.54 (1H, d), 8.15 (1H, s).

2-Adoc-D-MeTrp-L-Phe-L-Glu(OMe)$_2$ (5f)

L-Glutamic acid, N-[N-[α-methyl-N-[(tricyclo[3.3.1.1$^{3,7}$]dec-2-yloxy)carbonyl]-D-tryptophyl]-L-phenylalanyl[-, dimethyl ester

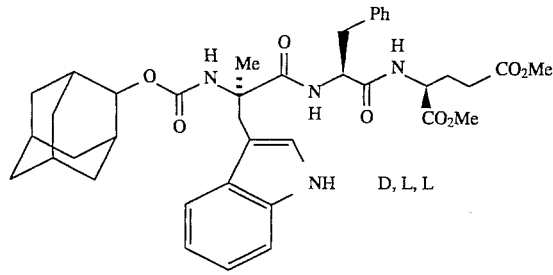

NMR (CDCl$_3$) δ 1.34 (3H, s), 1.73–2.36 (14H, m), 3.09 (2H, qd), 2.37 (2H, abq), 3.65 (3H, s), 3.71 (3H, s), 4.50 (1H, m), 4.68 (2H, m), 4.91 (1H, s), 6.38 (1H, d), 6.90–7.24 (10H, m), 7.34 (1H, d), 7.56 (1H, d), 8.15 (1H, s).

2-Adoc-D-MeTrp-L-Phe-NHCH(CO$_2$Et)$_2$ (5 g)

NMR (DMSO-d$_6$) δ 1.12 (3H, s), 1.22 (6H, m), 1.45 (2H, br.t), 1.68–2.00 (14H, m), 2.89–3.09 (3H, m), 4.20 (4H, m), 4.68 (2H, br.m), 5.09 (1H, d), 6.682 (1H, br.s), 6.87 (2H, br.s), 7.00 (1H, t), 7.17–7.38 (8H, m), 7.78 (1H, br.d), 8.78 (1H, br.d), 10.79 (1H, s).

Example 2

2-Adoc-D-MeTrp-L-Phe-L-Asp (6h)

L-Aspartic acid,
N-[N-[α-methyl-N-[(tricyclo[3.3.1.1$^{3,7}$]dec-2-yloxy)carbonyl]-D-tryptophyl]-L-phenylalanyl]-

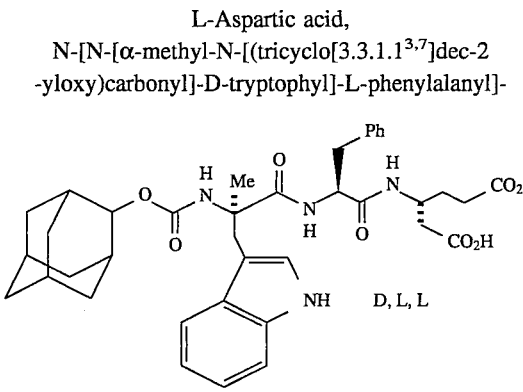

Similarly prepared was (6H) via the dibenzyl ester (5e).

2-Adoc-D-MeTrp-L-Phe-L-Asp (6h)

NMR (DMSO-D$_6$) δ 1.07 (3H, s), 1.38 (1H, d), 1.49 (2H, t), 1.60–2.09 (14H, m), 2.51–3.30 (6H, complex), 4.56 (2H, br.d), 4.74 (1H, s), 6.73–7.39 (10H, m), 7.83 (1H, d), 8.14 (1H, d), 10.83 (1H, s), 12.60 (1H, br); IR (CHBr$_3$ film) 1645, 1705 cm$^{-1}$.

Example 3

2-Adoc-D-MeTrp-L-Phe-Glu (6i)

L-Glutamic acid,
N-[N-[α-methyl-N-[(tricyclo[3.3.1.1$^{3,7}$]dec-2-yloxy)carbonyl]-D-tryptophyl]-L-phenylalanyl]-

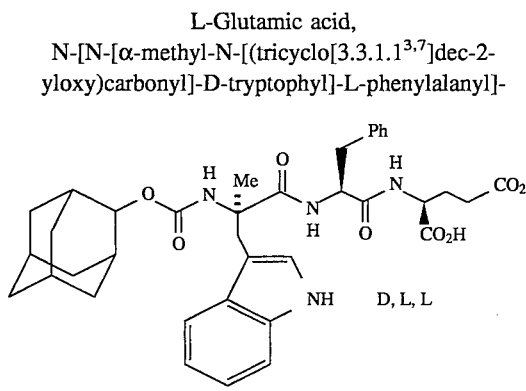

(6i) was prepared by slow saponification of the precursor methyl ester (5f) using 0.1N LiOH (or NaOH) in THF or dioxan.

NMR (DMSO-d$_6$) δ 1.08 (3H, s), 1.49 (2H, t), 1.70–2.05 (18H, m), 2.32 (2H, t), 2.93 (1H, dd), 3.08–3.50 (5H, m), 4.25 (1H, m), 4.68 (2H, br.m.), 6.78 (1H, br.s), 6.88–7.42 (11H, m), 7.83 (2H, br.d), 10.80 (1H, s), 12.40 (1H, br.s).

Example 4

2-Adoc-D-MeTrp-L-Phe-Gly (6j)

Glycine, N-[2-methyl-N-[(tricyclo[3.3.1.1$^{3,7}$]dec-2-yloxy)carbonyl]-D-tryptophyl]-L-phenylalanyl-

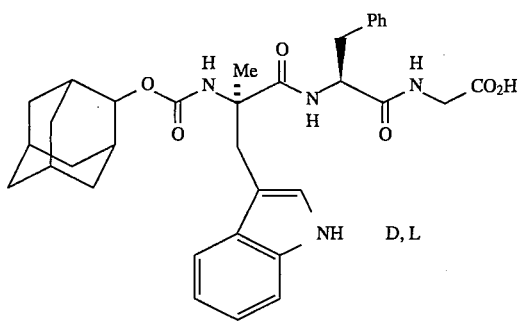

2-Adoc-D-MeTrpOPfp (1.68 g, 3.00 mmol) was added to a solution of PheGly (0.732 g, 3.30 mmol) and DIPEA (0.851 g, 6.60 mmol) in DMF (20 mL). After stirring overnight, the solvent was removed and the residue chromatographed on silica (10% MeOH/CH$_2$Cl$_2$+1% AcOH) giving 846 mg of a white solid (6i), 47%. NMR (DMSO-d$_6$) δ 1.15 (3H, s), 1.47 (2H, t), 1.68–2.00 (12, m), 2.93 (1H, dd), 3.20 (2H, dd), 3.17 (1H, m), 3.66 (2H, br.s), 4.60 (1H, m), 4.68 (1H, s), 6.72–7.41 (12H, m), 7.96 (1H, br.s), 10.85 (1H, s); IR (CHBr$_3$ film) 1665 cm$^{-1}$.

The following were prepared as in Scheme IA.

Example 5

β-Alanine,
N-[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-4-phenylbutyl]-, methyl ester, [R-(R*,S*)] (10a)

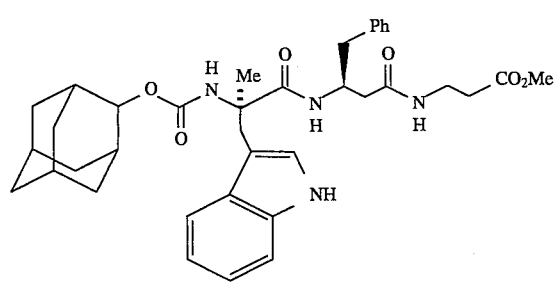

NMR (CDCl$_3$) δ 1.26 (3H, t), 1.37 (3H, s), 1.52 (2H, m), 1.71–2.01 (15H, m), 2.29 (1H, dd), 2.50 (1H, br.dd), 2.77 (2H, m), 3.30 (2H, s), 3.74 (1H, dd), 4.09–4.21 (3H, m), 4.42 (1H, m), 4.74 (1H, s), 5.16 (1H, s), 6.72 (1H, br.s), 6.91 (1H, s), 7.08–7.32 (10H, m), 7.57 (1H, d), 8.13 (1H, s).

Example 6

Glycine,
N-[3-[[3-(1H-indol-3-yl)-2-methyl-1-oxo-2-
[[(tricyclo[3.3.1.1$^{3,7}$
]dec-2-yloxy)carbonyl]amino]propyl]amino]-1-
oxo-4-phenylbutyl]-, ethyl ester, [R-(R*,S*)]- (10k)

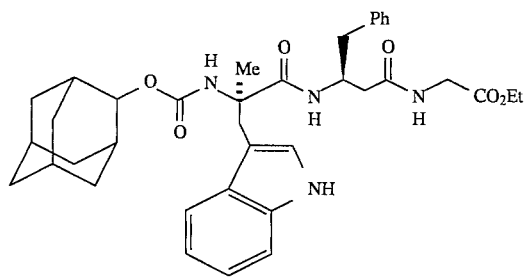

[R—(R*, S*)]

NMR (CDCl$_3$) δ 1.45 (3H, s), 1.52 (2H, br.d), 1.71–2.03 (16H, m), 2.22 (2H, qd), 2.52 (2H, t), 2.74 (2H, qd), 3.36 (2H, abq), 3.47 (2H, m), 3.69 (3H, s), 4.35 (1H, m), 4.80 (1H, br.s), 5.23 (1H, s), 6.27 (1H, br.t), 6.88 (1H, d), 7.04–7.33 (10H, m), 7.59 (1H, d), 8.25 (1H, s).

Example 8

β-Alanine,
N-[3-[[3-(1H-indol-3-yl)-2-methyl-1-oxo-2
-[[(tricyclo[3.3.1.1$^{3,7}$]dec-2-
yloxy)carbonyl]amino]propyl]amino]-1-oxo-4-
phenylbutyl]-, [R-(R*,S*)]-

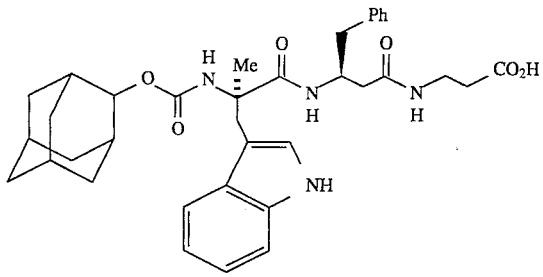

[R—(R*, S*)]

NMR (CDCl$_3$) δ 1.37 (3H, s), 1.50 (2H, br.d), 1.68–1.98 (16H, m), 2.27 (2H, m), 2.73 (2H, m), 3.24 (2H, q), 3.76 (1H, dd), 4.04 (1H, dd), 4.38 (1H, m), 4.74 (1H, s), 4.90 (1H, br.s), 6.83 (1H, s), 7.02–7.19 (10H, m), 7.29 (1H, d), 7.52 (1H, d), 8.52 (1H, br.s).

Example 7

2-Adoc-D-MeTrp-L-NHCH(CH$_2$Ph)CH$_2$CO-
GABA-OEt (10l) L-Phenylalaninamide,
α-methyl-N-[(tricyclo[3.3.1.1$^{3,7}$]dec-2-
yloxy)carbonyl]-L-tryptophyl-N-(4-ethoxy-4-oxobutyl)-

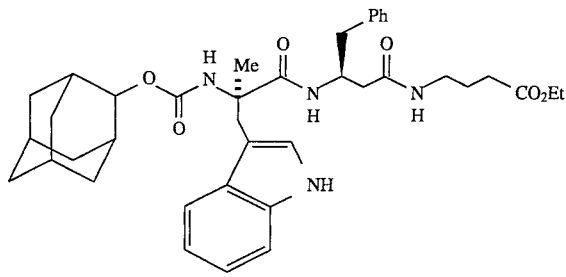

D, L

NMR (CDCl$_3$) δ 1.24 (3H, 5), 1.45 (3H, s), 1.51 (2H, br.d), 1.71–2.01 (16H, m), 2.21 (2H, qd), 2.33 (2H, t), 2.74 (2H, qd), 3.21 (2H, m), 3.36 (2H, q), 4.11 (2H, q), 4.36 (1H, m), 4.79 (1H, br.s), 5.22 (1H, s), 6.05 (1H, br.t), 6.89 (1H, d), 7.03–7.33 (10H, m), 7.58 (1H, d), 8.38 (1H, s).

Example 9

Glycine,
N-[3-[[3-(1H-indol-3-yl)-2-methyl-1-oxo-2-
[[(tricyclo[3.3.1.1$^{3,7}$
]dec-2-yloxy)carbonyl]amino]propyl]amino]-4-
phenylbutyl]-, [R-(R*,S*)]- (11k)

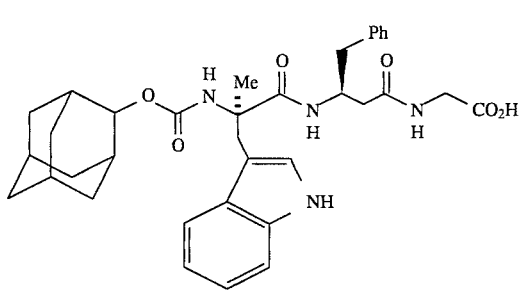

[R—(R*, S*)]

NMR (DMSO-d$_6$) δ 1.15 (3H, s), 1.47 (2H, t), 1.59–1.97 (16H, m), 2.20 (2H, m), 2.37 (2H, t), 2.72 (2H, m), 3.22 (4H, m), 4.22 (1H, m), 4.66 (1H, br.s), 6.81 (2H, s), 6.89 (1H, t), 7.01 (1H, t), 7.03–7.30 (6H, m), 7.42 (1H, d), 7.79 (1H, d), 7.96 (1H, br.s), 10.87 (1H, s).

Example 10

2-Adoc-D-MeTrp-L-NHCH(CH₂Ph)CH₂CO-GABA
(111)

Butanoic acid,
4-[[3-[[3-(1H-indol-3-yl)-2-methyl-1-oxo-2-
[[(tricyclo[3.3.1.1³,⁷]dec-2-
yloxy)carbonyl]amino]propyl]amino]-1-oxo-4-
phenylbutyl]amino]-, [R-(R*,S*)]-

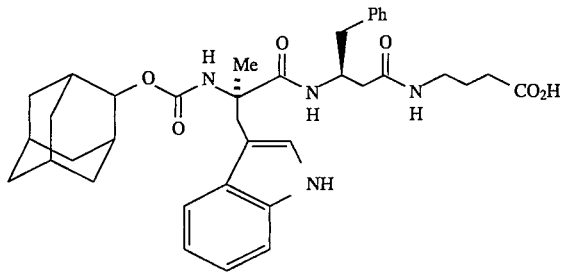

[R—(R*, S*)]

NMR (CDCl₃) δ 1.42 (3H, s), 1.51 (2H, d), 1.70–2.00 (14H, m), 2.21 (2H, m), 2.34 (2H, t), 2.76 (2H, m), 3.21 (2H, m), 3.30 (2H, q), 4.37 (1H, m), 4.79 (1H, s), 5.30 (1H, s), 6.43 (1H, br.s), 6.90 (1H, s), 6.99–7.33 (12H, m), 7.55 (1H, d), 8.52 (1H, s).

Example 11

2-[[3-(1H-indol-3-yl)-2-methyl-1-oxo-2-
[[tricyclo[3.3.1.1³,⁷
]dec-2-yloxy)carbonyl]amino]-propyl]amino]-3-
phenylpropyl[R-(R*,S*)]-1,4-dihydro-1-methyl-3
-pyridinecarboxylate

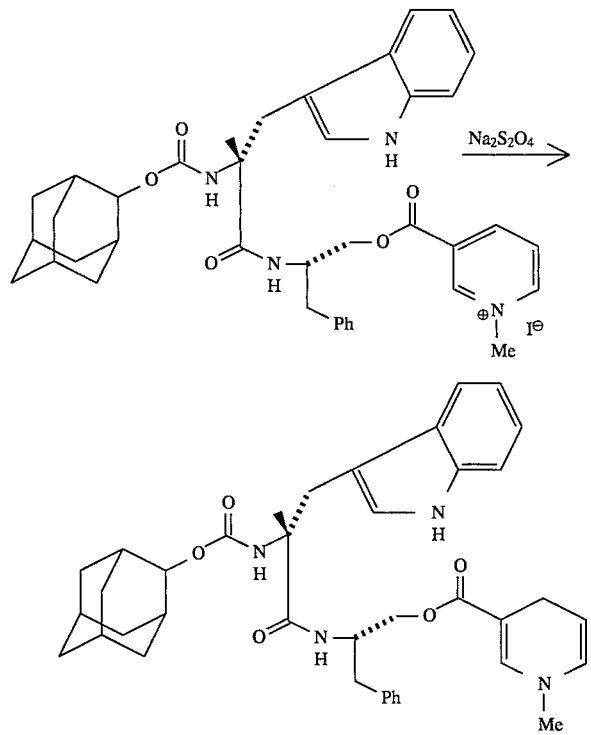

A solution of the pyridinium salt (150 mg, 0.193 mmol) dissolved in dichloromethane (10 mL) was stirred at 5° C. (internal temperature) with a Na₂HPO₄/KH₂PO₄ buffer solution (pH 7.0, 10 mL) while nitrogen was bubbled through the solution for 30 minutes to deaerate the system. Sodium dithionite (335 mg, 1.93 mmol, 10 equiv.) was added in one portion and the mixture stirred under a nitrogen atmosphere for 3 hours. The layers were separated, the aqueous and the combined organic phases washed with cold deaerated water, dried (MgSO₄), filtered, and concentrated to a yellow resin. Chromatographic purification of this crude product (reverse phase, LiChroprep RP18, Merck 13900, MeOH:H₂O, 4:1) gave the title compound as a yellow powder (44 mg, 35%); m.p. 116°–121° C. (amorphous); δ (CDCl₃); 1.49–2.05 (17H, m, adamantyl H̲ and quaternary C H̲₃), 2.57 (1H, dd, J=8.4 Hz, 13.6 Hz), and 2.81 (1H, dd, J=5.3 Hz, 13.6 Hz, PhCH̲₂), 2.90 (3H, s, NCH̲₃), 3.04 (2H, br s, pyr C(4)H̲) 3.33 (1H, d, J=14.8 Hz) and 3.42 (1H, d, J=14.8 Hz, CH̲₂indole), 3.93 (1H, dd, J=3.9 Hz, 11.5 Hz) and 4.03 (1H, dd, J=5.4 Hz, 11.5 Hz, CH̲₂OCOpyr), 4.28 (1H, m, CHmethine), 4.76 (1H, dt, J=4.2 Hz, 8.0 Hz, pyr C(5)H̲), 4.80 (1H, br s, adamantyl C(2)H̲), 5.32 (1H, br s, carbamate, CONH̲), 5.61 (1H, dd, J=1.6 Hz, CONH̲), 6.92 (1H, d, J=2.3 Hz, indole C(2)H̲), 6.95 (1H, d, J=1.4 Hz, pyr C(2)H̲), 7.06–7.33 (8H, m, PhH̲ and indole C(5)H̲, C(6)H̲ and C(7)H̲), 7.61 (1H, d, J=7.7 Hz, indole C(4)H̲), 8.22 (1H, br s, indole NH̲); ν_{max} (nujol mull), 3326, 1664, 1593, 1497 cm⁻¹.

EXAMPLE 12

2-[[3-(1H-indol-3-yl)-2-methyl-1-oxo-2-[[tricyclo-
[3.3.1.1³,⁷]dec-2
-yloxy)carbonyl]amino]-propyl]amino]-3-
phenylpropyl[R-(R*,S*)]-trigonelline iodide

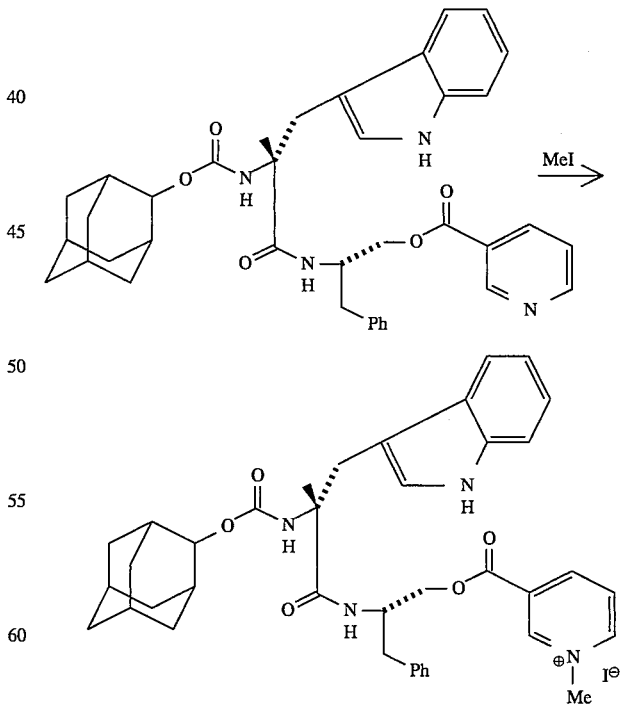

A solution of the nicotinate ester (186 mg, 0.29 mmol) in nitromethane (2mL) containing iodomethane (0.5 mL, excess) was stirred in a stoppered flask at room temperature for 24 hours, concentrated in vacuo with addition of ether to precipitate material as a solid and dried at 50° C. in vacuo, leaving the title compound as a yellow powder (220 mg, 98%); m.p. 132°–136° C.; δ (DMSO-d$_6$), 1.10 (3H, s, quaternary (3H, s, CH$_2$Ph and one CH$_2$indole), 3.31–3.49 (2H, m, one CH$_2$ indole and NH), 4.23 (2H, dd, J=8.0 Hz, 10.0 Hz, CH$_2$OCOpyr), 4.44 (3H, s, N$^+$CH$_3$), 4.49 (2H, m, adamantyl C(2)H and CH methine), 6.83–6.91 (3H, m, indole C(5 or 6)H, C(2)H, amide CONH), 7.00 (1H, apparent t, J=7.5 Hz, indole C(5 or 6)H, 7.20–7.31 (6H, m) and 7.22 (1H, d, J=2.3 Hz, PhH and indole C(4)H, C(7)H), 7.81 (1H, d, J=8.8 Hz, indole NH), 8.28 (1H, dd, J=7 Hz, pyr C(5)H), 9.01 (1H, d, J=2 Hz, pyr C(4)H), 9.18 (1H, d, J=6.2 Hz, pyr C(6)H), 9.51 (1H, s, pyr C(2)H), $v^{max}$ (mull) 3628, 1738, 1702, 1658, 1496 cm$^{-1}$; α$_D$=+60.2° C. (MeOH, C, 0.01); m/e (found) 649.3386 C$_{39}$H$_{45}$N$_4$O$_5$ (excluding I$^-$) requires m/e 649.3386 C$_{39}$H$_{45}$N$_4$O$_5$I.2H$_2$O requires C, 57.63; H, 6.07; N, 6.89. Found; C, 57.88; H, 6.35; N, 6.90.

EXAMPLE 13

2-[3-[3-(1H-indol-3-yl)-2-methyl-1-oxo-2-[[(tricyclo-[3.3.1.1$^{3,7}$]dec-2-yloxy)carbonyl]amino]-propyl]amino]-3-phenylpropyl[R-(R*,S*)]-3-pyridine-carboxylate

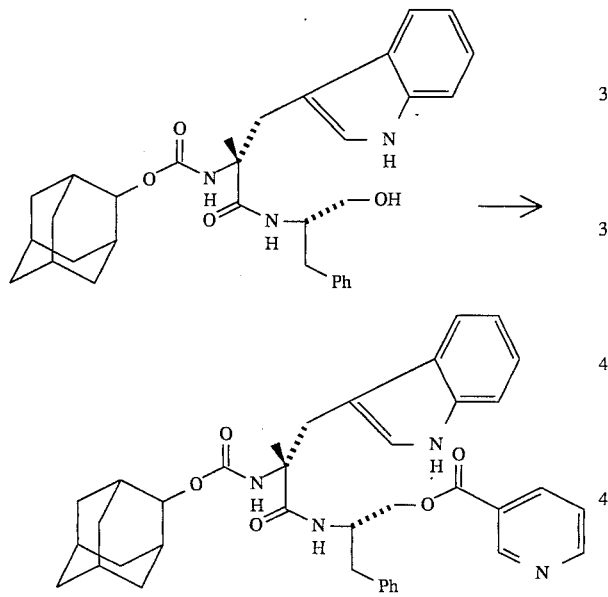

To a solution of the alcohol (377 mg, 0.71 mmol), DMAP (8 mg, 0.07 mmol, 0.1 equiv.) and nicotinic acid (88 mg, 0.71 mmol, 1 equiv.) in dry dichloromethane (8 mL) was added N,N'-dicyclohexylcarbodiimide (154 mg, 0.74 mmol, 1.05 equiv.), and the mixture stirred at room temperature for 16 hours. The opaque mixture was then diluted with ether, filtered, concentrated to a white resin and chromatographically purified (reverse phase, MeOH:H$_2$O, solid); (307 mg, 68%); m.p. 86°–88° C.; δ (CDCl$_3$) 1.45–1.90 (17H, m, adamantyl H and quaternary CH$_3$), 2.73 (1H, dd, 13.7 Hz, 7.8 Hz), and 2.88 (1H, dd, J=6.2 Hz), 13.7 Hz, CH$_2$Ph), 3.24 (1H, d, J=14.7 Hz) and 3.48 (1H, d, J=14.7 Hz, CH$_2$ indole), 4.23 (2H, d, J=4.8 Hz, CH$_2$OCO pyr), 4.53 (1H, m, CH methine), 4.71 (1H, m, adamantyl C(2)H), 5.20 (1H, s, carbamate OCONH), 6.79 (1H, d, J=8.1 Hz, amide CONH), 6.93 (1H, d, J=2.2 Hz, indole C(2)H, C(7)H), 7.35 (1H, dd, J=7.9 Hz, 4.7 Hz, pyr C(5)H), 7.67 (1H, d, J=7.8 Hz, indole C(4)H), 8.22 (1H, dt, J=1.8 Hz, 8.0 Hz, pyr C(4)H), 8.46 (1H, m, indole NH), 8.76 (1H, dd, J=3.2 Hz, 4.8 Hz, pyr C(6)H, 9.16 (1H, d, J=1.7 Hz, pyr C(2)H), $v_{max}$ (mull) 3320, 1719, 1660 cm$^{-1}$; α$_D$=+31.2° C. (CHCl$_3$, , CiO 0.006); C$_{38}$H$_{42}$N$_4$O$_5$ requires C, 71.90; H, 6.67; N, 8.82%. Found: C, 71.45; H, 6.66; N, 8.73%.

EXAMPLE 14

Butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-, (2,2-dimethyl-1-oxopropoxy)methyl ester, [R-(R*,R*)]-

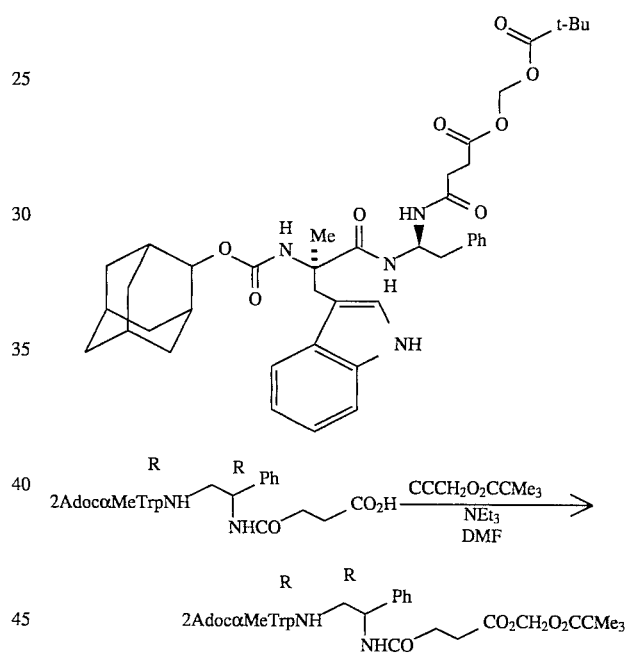

To a solution of the above acid (500 mg) in DMF (5 mL) was added NEt$_3$ (117 mg) followed by CCCH$_2$O$_2$CCMe$_3$ (247 mg). The reaction mixture was stirred for 5 days at room temperature and then poured into H$_2$O. The product was extracted with EtOAc and the organic layer dried (MgSO$_4$) and concentrated to yield a gum (750 mg).

The crude product was purified by column chromatography (50% to 75% EtOAc/hexane) to yield the desired dilute ester (2) as an amorphous white solid (120 mg), mp 110°–116° C.; IR (film) 3317, 3061, 1757, 1700, 1666 cm$^{-1}$; $^1$HNMR (d$^6$l-DMSO) δ 1.12 (12H, brs), 1.49 (2H, brs) 1.60–2.05 (12H, m), 2.50 (4H, m, observed by DMSO), 3.20–3.40 (4H, m, observed by H$_2$O), 4.69 (1H, brs), 4.96 (1H, m), 5.65 (2H, s), 6.72 (1H, brs), 6.93 (2H, brs), 7.01 (1H, t, J 8 Hz), 7.30 (6H, m), 7.43 (1H, d, J 8 Hz), 7.74 (1H, t, J 4 Hz), 8.16 (1H, brs), 10.86 (1H, s).

EXAMPLE 15

Butanoic acid,
4-[[2-[[3-(1H-indol-3-yl)-2-methyl-1-oxo-2-
[[tricyclo[3.3.1.1$^{3,7}$]dec-2-
yloxy)carbonyl]amino]propyl]amino]ethyl]amino]-
4-oxo-, chloromethyl ester, [R-(R*,R*)]-

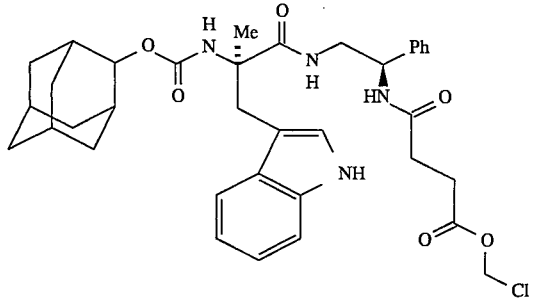

To a suspension of [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid (CI-988) (500 mg, 0.81 mmol), sodium hydrogen carbonate (240 mg, 2.86 mmol), and tetrabutyl ammonium hydrogen sulphate (28 mg, 0.08 mmol) in CH$_2$Cl$_2$ (5 mL) and water (5 mL) was added dropwise a solution of chloromethyl sulphonyl chloride (163 mg, 0.99 mmol) in CH$_2$Cl$_2$ (3 mL). The mixture was stirred at room temperature for 5 hours and then 10% citric acid solution and CH$_2$Cl$_2$ were added. The organic phase was separated, dried (MgSO$_4$), filtered, and evaporated. Purification by column chromatography on silica gel eluting with ethyl acetate/hexane mixtures gave butanoic acid, 4-[[2-[[3-(1H-indol-3-yl)-2-methyl-1-oxo-2-[[(tricyclo[3.3.1.1$^{3,7}$ ]dec-2-yloxy)carbonyl]amino]propyl]amino]ethyl]amino]-4-oxo-, chloromethyl ester, [R-(R*,R*)]- as an amorphous white solid (343 mg, 52%), mp 155°–122° C. 300 MHz NMR (CDCl$_3$ δ 1.42 (s, 3H), 1.50–1.60 (m, 2H), 1.70–2.00 (m, 12H), 2.55–2.80 (m, 4H), 3.25–3.40 (m, 3H), 3.47 (d, J 14.6 Hz, 1H), 4.00–4.15 (m, 1H), 4.89 (s, 1H), 5.20–5.30 (m, 2H), 5.60–5.70 (m, 2H), 6.30–6.40 (m, 1H), 6.95 (d, J 2.3 Hz, 1H), 7.05–7.40 (m, 10H), 7.56 (d, J 7.8 Hz, 1H), 8.46 (s, 1H).

Analysis for C$_{36}$H$_{43}$ClNO$_6$·0.5H$_2$O. Calcd: C, 64.32; H, 6.59; N, 8.33. Found: C, 64.14; H, 6.45, N, 8.23.

EXAMPLE 16

Pentanedioic acid,
[4-[[2-[[3-(1H-indol-3-yl)-2-methyl-1-oxo-2-
[[(tricyclo[3.3.1.1$^{3,7}$]dec-2-
yloxy)carbonyl]amino]propyl]amino]-1-
phenylethyl]amino]-1,4-dioxobutoxy]methyl ester,
[R-(R*,R*)]-, compd. with
1-deoxy-1-(methylamino)-D-glucitol

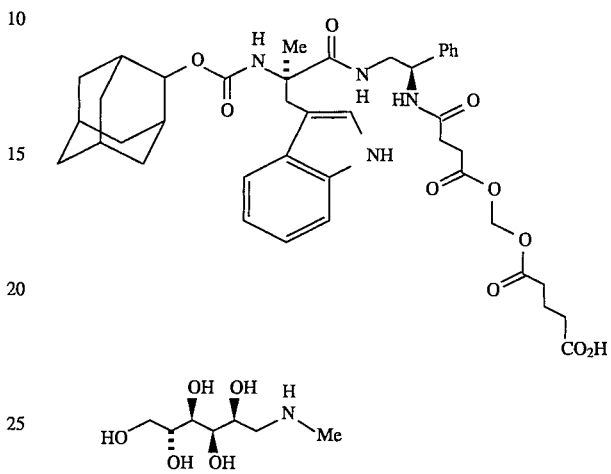

A. To a solution of glutaric acid monobenzyl ester (170 mg, 0.77 mmol) in CH$_2$Cl$_2$ (5 mL) and water (5 mL) was added tetrabutyl ammonium hydrogen sulphate 26 mg, 0.077 mmol) and sodium hydrogen carbonate (225 mg, 2.68 mmol), followed by chloromethyl sulphonyl chloride (153 mg, 0.93 mmol) in CH$_2$Cl$_2$ (3 mL). The reaction mixture was stirred at room temperature for 3 hours and then citric acid solution added and the organic phase separated, washed, dried, and evaporated to give a colorless oil (220 mg, 106%). 300 MHz NMR (CDCl$_3$) δ 1.9–2.05 (m, 2H), 2.4–2.5 (m, 4H), 5.12 (s, 2H, CH$_2$), 5.68 (s, 2H, CH$_2$), 7.3–7.4 (m, 5H).

B. To a solution of CI-988 (222 mg, 0.36 mmol) in DMF (5 mL) was added triethylamine (55 mg, 0.54 mmol), followed by chloromethyl benzyl glutarate (146 mg, 0.54 mmol). After 9 days ethyl acetate and water were added and the organic phase separated, washed, dried, and evaporated to give a yellow gum. Purification by column chromatography on silica gel, eluting with ethyl acetate hexane mixtures, gave the product as an amorphous solid (110 mg, 36%). 300 MHz NMR (CDCl$_3$) δ 1.45 (s, 3H), 1.50–2.00 (m, 16H), 2.30 –2.70 (m, 8H), 3.30–3.40 (m, 2H), 3.48 (d, J 14.7, 1H), 3.90–4.05 (m, 1H), 4.86 (s, 1H), 5.05–5.15 (m, 5H), 5.70–5.75 (m, 2H), 6.30–6.40 (m, 1H), 6.99 (d, J 2.1 Hz, 1H), 7.10–7.40 (m, 16H), 7.58 (d, J 7.7, 1H), 8.32 (s, 1H).

C. The benzyl ester from B (110 mg, 0.13 mmol) was dissolved in ethanol (50 mL) and hydrogenated over Pearlman's catalyst (10 mg) at 45 psi for 4 hours. The solution was filtered to remove catalyst and evaporated to dryness to give an amorphous solid (105 mg, 100%). 300 MHz NMR DMSO δ 1.19 (s, 3H), 1.40–2.00 (m, 14H), 2.23 (6, J 7.3 Hz, 2H), 2.36 (t, J 7.4 Hz, 2H), 2.40–2.60 (m, obscured by DMSO), 3.10–3.40 (m, obscured by water), 4.68 (s, 1H), 4.95–5.00 (m, 1H), 5.65 (s, 2H), 6.77 (bs, 1H), 6.85–6.95 (m, 2H), 7.01 (t, J 7.7 Hz, 1H), 7.20–7.35 (m, 7H), 7.43 (d, J 7.8 Hz, 1H), 7.84 (bs, 1H), 8.23 (bs, 1H).

Analysis calculated for $C_{48}H_{67}N_5O_{10}\cdot H_2O$. Calcd: C, 59.30; H, 7.15; H, 7.20. Found: C, 58.85; H, 7.11; N, 7.08.

6H), 3.25–3.35 (m, 2H), 3.46 (d, J 14.6 Hzβ, 1H), 3.95–4.05 (m, 1H), 4.85 (s, 1H), 5.04 (s, 1H), 5.10–5.20 (m, 1H), 6.30–6.40 (m, 1H), 6.77 (d, J 8.1 Hz, 1H), 6.87 (s, 1H), 6.97 (d, J 2.3 Hz, 1H), 7.05–7.25 (m, 8H), 7.32 (d, J 7.9 Hz, 1H), 7.56 (d, J 8.0 Hz, 1H), 8.24 (s, 1H).

Analysis calculated for $C_{44}H_{50}N_4O_6\cdot H_2O$ Calcd: C, 70.56; H, 7.00; N, 7.48. Found: C, 70.80; H, 6.81; N, 7.54.

EXAMPLE 18

Butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-, 2-(diethylamino)ethyl ester, [R-(R*,R*)]-

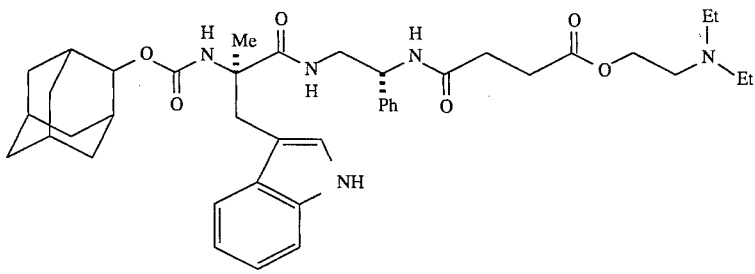

EXAMPLE 17

Butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-2,3-dihydro-1H-inden-5-yl ester, [R-(R*,R*)]-

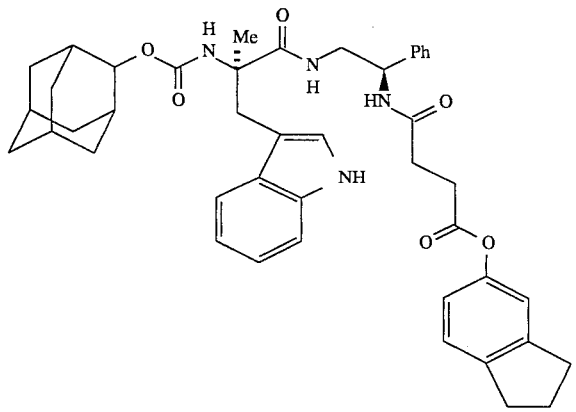

To a solution of CI-988 (200 mg, 0.33 mmol) in DMF (5 mL) was added 5-indanol (44 mg, 0.33 mmol), BOP reagent (158 mg, 0.36 mmol), and diisopropylethylamine (92 mg, 0.71 mmol). After stirring for several weeks at room temperature the reaction mixture was poured onto 10% citric acid solution and extracted with ethyl acetate to give a brown gum (175 mg). Purification by column chromatography on silica, eluting with hexane/ethyl acetate 4:6 gave butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-2,3 -dihydro-1H-inden-5-yl ester, [R-(R*,R*)]- as an amorphous solid (38 mg, 16%), mp 93°–98° C. 300 MHz NMR (CDCl$_3$) δ 1.43 (s, 3H, 1.45–2.10 (m, 16H), 2.55–2.70 (m, 2H), 2.80–3.00 (m, To a cooled solution of CI-988 in DMF (40 mL) was added dimethyl amino pyridine (32 mg, 0.26 mmol), diethylethanolamine (0.60 g, 5.12 mmol), and then dicyclohexylcarbodiimide (0.528 g, 2.56 mmol). After allowing the reaction to warm up slowly to room temperature overnight, the reaction was stirred at room temperature for 3 days. The reaction was poured onto ethyl acetate and water. The organic phase was separated, washed with water, dried (MgSO$_4$), filtered, and solvents evaporated to give an oil. Purification by column chromatography on silica gel, eluting with ethyl acetate/hexane 3:2 gave the product as a pale pink sold, mp 115°–120° C. 300 MHz NMR (CDCl$_3$) δ 0.85–2.00 (m, 29H), 2.55–2.80 (m, 4H), 3.20–3.30 (m, 1H), 3.30–3.45 (m, 2H), 3.50–3.60 (m, 1H), 3.80–3.95 (m, 1H), 4.05–4.20 (m, 1H), 4.83 (s, 1H), 4.90–5.00 (m, 1H), 5.25 (s, 1H), 6.30–6.40 (m, 1H), 7.00–7.25 (m, 8H), 7.40 (d, J 8.0 Hz, 1H), 7.50–7.60 (m, 2H), 9.05 (s, 1H).

Microanalysis calculated for $C_{41}H_{55}N_5O_6$. Calcd: C, 68.91; H, 7.76; N, 9.81. Found: C, 69.29; H, 8.06; N, 9.90.

We claim:

1. A compound of the formula

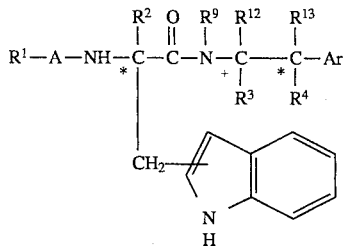

or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, CO$_2$R*, CF$_3$, NR$^5$R$^6$, and —(CH$_2$)$_n$OR$^5$ wherein R* is hydrogen, straight or branched alkyl of from one to six carbon atoms, —(CH$_2$)$_n$Ar, —COAr, —(CH$_2$)$_n$OCOAr, or —(CH$_2$)$_n$NR$^5$COAr and R* may also independently be R as defined below, and R must be present once in formula I, and R is attached to formula I through a metabolically labile bond, R$^5$ and R$^6$ are each independently hydrogen or alkyl of from one to six carbon atoms and n is an integer from zero to six; and R is —(CH$_2$)$_n$NR$^5$R$^6$, —(CH$_2$)$_n$—B—D* wherein D* is O—COR*, CO$_2$Ar$^2$, (CH$_2$)$_n$Ar$^2$, OCOAr$^2$, NR$^5$COAr$^2$, COAr$^2$, CO$_2$CH(R)—CO$_2$R*, CO$_2$—(CH$_2$)$_n$OCOR* where Ar$^2$is independently taken from Ar, where m is as defined below, CONHCH(R)CO$_2$R* where R is a side chain of aspartic or glutamic acid, R is hydrogen only when B is not a bond, —CO$_2$CH$_2$CH$_2$N$^+$(R*)$_3$X$^{1-}$ when X$^{1-}$ is a pharmaceutically acceptable counter anion, A is —(CH$_2$)$_n$CO—, —SO$_2$—, —S(=O)—, —NHCO—, —(CH$_2$)$_n$—C(=O)—,

—O—(CH$_2$)$_n$CO— or —HC=CHCO— wherein n is an integer from zero to six;

R$^2$ is CH$_3$;

R$^3$ and R$^4$ are each independently selected from hydrogen, R$^2$ and —(CH$_2$)$_{n'}$, —B—D wherein:

n' is an integer of from zero to three;

B is a bond,
—OCO(CH$_2$)$_n$—,
—O(CH$_2$)$_n$—,
—NHCO(CH$_2$)$_n$—,
—CONH(CH$_2$)$_n$—,
—NHCOCH=CH—,
—COO(CH$_2$)$_n$—,
—CO(CH$_2$)$_n$—,
—S—(CH$_2$)$_n$—,
—S(=)—(CH$_2$)$_n$—,
—SO$_2$—(CH$_2$)$_n$—,
—NHSO$_2$—(CH$_2$)$_n$—,
—SO$_2$NH—(CH$_2$)$_n$—,

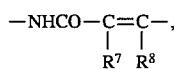

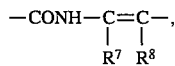

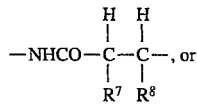

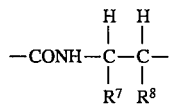

wherein R$^7$ and R$^8$ are each independently selected from hydrogen and R$^2$ or together form a ring (CH$_2$)$_m$ wherein m is an integer of from 1 to 5 and n is as defined above;

D is hydrogen,
—COOR*,
—CH$_2$NR$^5$R*,
—CHR$^2$NR$^5$R*,
—CH$_2$OR*,
—CHR$^2$OR*,

—CH$_2$SR*,
—CHR$^2$SR*,
—CONR$^5$R$^6$,
—CONR$^5$R*, an acid replacement selected from

HO$_3$S—\},

\}—PO$_3$H$_2$—,

PhSO$_2$NHCO—\},

CF$_3$CONHCO—\},

CF$_3$SO$_2$NHCO—\},

H$_2$NSO$_2$—\}, wherein R*, R$^2$, R$^5$, and R$^6$ are as defined above;

R$^9$ is hydrogen or a straight or branched alkyl of from one to six carbon atoms, —(CH$_2$)$_n$CO$_2$R*, —(CH$_2$)$_n$NR$^5$R*, wherein n, R*, and R$^5$ are as defined above or taken from R$^3$;

R$^{12}$ and R$^{13}$ are each independently hydrogen or are each independently taken with R$^3$ and R$^4$, respectively, to form a moiety doubly bonded to the carbon atom; and Ar is a mono- or polycyclic unsubstituted or substituted carbo- aromatic or carbo- hydroaromatic moiety.

2. A compound according to claim 1 wherein the cycloalkyl or polycycloalkyl has from about six to about ten carbon atoms.

3. A compound according to claim 1 wherein each substituent on the cycloalkyl or polycycloalkyl is independently R*, F, Cl, Br, OR*, NR$^5$R*, CF$_3$.

4. A compound according to claim 1 wherein the polycycloalkyl is selected from the group consisting of

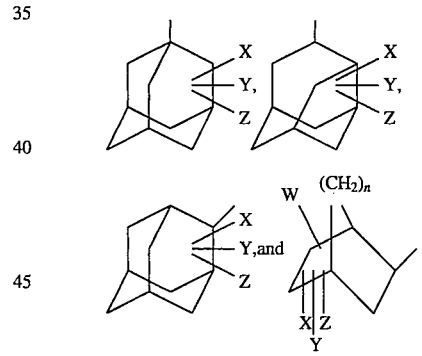

wherein W, X, Y, and Z are each independently hydrogen, a straight or branched alkyl of from one to six carbon atoms, CF$_3$, NR$^5$R$^6$, —(CH$_2$)$_n$CO$_2$R*, CN, F, Cl, Br, OR*, SR*, wherein R*, R$^5$ and R$^6$ are as defined in claim 1 and n is an integer of from 1 to 3.

5. A compound according to claim 1 wherein A is —NHCO—, OC(=O)—, —SO$_2$—, —S(=O)—, —SCO— or —CH$_2$CO—.

6. A compound according to claim 1 wherein Ar is an unsubstituted or substituted phenyl whose substituents are each independently selected from hydrogen, fluorine, chlorine, bromine, iodine, methyl, methoxy, trifluoromethyl, nitro, —NHCOCH2COOH, and —CH2CH2CO2H.

7. A compound according to claim 1 wherein:

R$^1$ is 2-adamantyl or 1-(S)-2-endobornyl;

A is —NHCO—, —OCO—, —SO$_2$—, —S(=O)— or —CH$_2$CO—;

R$^2$ is —CH$_3$, —CH$_2$CO$_2$H or —CH$_2$C≡CH;

$R^3$ is —$(CH_2)_n$, —B—D or H;
$R^4$ is —$(CH_2)_n$, —B—D or H;
$R^9$ is hydrogen or methyl.

8. A compound according to claim 1 wherein:
$R^1$ is 2adamantyl or 1-(S)-2-endobornyl;
A is —OC(=O)—;
$R^2$ is —$CH_3$;
$R^3$ is H, $CH_2OR^*$, $CH_2OCOCH_2CH_2CO_2R^*$, $CH_2OCOCH=CHCO_2R^*$, $CH_2NHCOCH_2CH_2CO_2R^*$, or $CH_2NHCOCH=CHCO_2R^*$,
$R^4$ is H, —$NHCOCH_2CH_2CO_2R^*$([D] configuration) or $NHCOCH=CHCO_2R^*$([D] configuration).

9. A compound according to claim 1 named butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo, (2,2-dimethyl-1-oxopropoxy)methyl ester [R-(R*,R*)]—.

10. A compound named butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]ethyl]amino]-4-oxo-, chloromethyl ester, [R-(R*,R*)]—.

11. A compound according to claim 1 named Pentanedioic acid, [4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-1,4-dioxobutoxy]methyl ester, [R-(R*,R*)]—.

12. A compound according to claim 1 named butanoic acid, 4-[[2-[[3-(1H-indol-3-yl)-2-methyl-1-oxo-2-[[tricyclo[3.3.1.1$^{3,7}$]dec-2-yloxy)carbonyl]amino]propyl]amino]-1-phenylethyl]amino]-4-oxo-2,3-dihydro- 1H-inden-5-yl ester, [R-(R*,R*)]—.

13. A compound according to claim 1 named butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-, 2-(diethylamino)ethyl ester [R-(R*,R*)]—.

14. A compound according to claim 1 named L-Aspartic acid, N-[N-[α-methyl-N-[(tricyclo[3.3.1.1$^{3,7}$]-dec-2-yloxy)carbonyl]-D-tryptophyl]-L-phenylalanyl]—.

15. A compound according to claim 1 named L-Glutamic acid, N-[N-[α-methyl-N-[(tricyclo[3.3.1.1$^{3,7}$]-dec-2-yloxy)carbonyl]-D-tryptophyl]-L-phenylalanyl]—.

16. A compound according to claim 1 named L-Glutamic acid, N-[N-[α-methyl-N-[(tricyclo[3.3.1.1$^{3,7}$]-dec-2-yloxy)carbonyl]-D-tryptophyl]-L-phenylalanyl]—, dimethyl ester.

17. A pharmaceutical composition comprising an amount of a compound according to claim 1 effective to treat gastrointestinal ulcers, psychotic behavior, to block the reaction caused by withdrawal from drug or alcohol use, to potentiate the effects of morphine or other opioids in treating pain, to suppress appetite, to reduce gastric acid secretion, to reduce anxiety, to treat and/or prevent panic in a mammal, and a pharmaceutically acceptable carrier.

* * * * *

UNITED STATES PATENT AND TRADEMARK OFFICE
CERTIFICATE OF CORRECTION

PATENT NO. : 5,554,643
DATED : September 10, 1996
INVENTOR(S) : Horwell et al.

It is certified that error appears in the above-indentified patent and that said Letters Patent is hereby corrected as shown below:

Column 46, line 52, delete the * and insert instead a ╬ (twice).

Column 47, line 39, inside the first parentheses should be =O.

Column 48, line 62, delete the second word and insert instead $-NH-\underset{\underset{O}{\|}}{C}-CH_2CH_2-COOH$ --.

Column 48, line 62, in the last word all the 2's should be subscripts.

Column 49, line 6, insert hyphen between 2 and adamantyl.

Signed and Sealed this

Eighteenth Day of March, 1997

Attest:

BRUCE LEHMAN

Attesting Officer        Commissioner of Patents and Trademarks